United States Patent
Yachi

(10) Patent No.: US 10,339,686 B2
(45) Date of Patent: Jul. 2, 2019

(54) IMAGE PROCESSING DEVICE, ENDOSCOPE APPARATUS, AND IMAGE PROCESSING METHOD

(71) Applicant: OLYMPUS CORPORATION, Hachioji-shi, Tokyo (JP)

(72) Inventor: Akikazu Yachi, Tokorozawa (JP)

(73) Assignee: OLYMPUS CORPORATION, Tokyo (JP)

(*) Notice: Subject to any disclaimer, the term of this patent is extended or adjusted under 35 U.S.C. 154(b) by 104 days.

(21) Appl. No.: 15/582,543

(22) Filed: Apr. 28, 2017

(65) Prior Publication Data

US 2017/0236317 A1 Aug. 17, 2017

Related U.S. Application Data

(63) Continuation of application No. PCT/JP2014/078974, filed on Oct. 30, 2014.

(51) Int. Cl.
*H04N 7/18* (2006.01)
*G06T 11/60* (2006.01)
(Continued)

(52) U.S. Cl.
CPC .......... *G06T 11/60* (2013.01); *A61B 1/00009* (2013.01); *A61B 1/04* (2013.01);
(Continued)

(58) Field of Classification Search
CPC ....... G06T 11/60; A61B 1/00009; A61B 1/06; A61B 1/04; A61B 1/0646; H04N 5/2356;
(Continued)

(56) References Cited

U.S. PATENT DOCUMENTS 5,148,502 A 9/1992 Tsujiuchi et al.
9,462,191 B2 * 10/2016 Ogasawara .......... H04N 5/2351
(Continued)

FOREIGN PATENT DOCUMENTS

| JP | 01309478 A | 12/1989 |
|---|---|---|
| JP | 10262176 A | 9/1998 |
| JP | 2013084152 A | 5/2013 |

OTHER PUBLICATIONS

Rana et al, Multiview depth map enhancement by variational bayes inference estimation of dirichlet mixture models (Year: 2013).*
(Continued)

*Primary Examiner* — Shan E Elahi
(74) *Attorney, Agent, or Firm* — Holtz, Holtz & Volek PC

(57) ABSTRACT

An image processing device includes a processor including hardware, the processor being configured to implement an image acquisition process that acquires captured images from an imaging section that performs a frame sequential imaging process in which one cycle includes first to N-th frames, and a synthesis process, wherein the processor implements the image acquisition process that acquires a plurality of captured images that have been captured in an i-th frame and differ from each other as to an in-focus object plane position, and the processor implements the synthesis process that calculates a second synthesis map based on a first synthesis map calculated with respect to the i-th frame, and the first synthesis map calculated with respect to a k-th frame, and synthesizes the plurality of images that have been captured in the i-th frame based on the second synthesis map.

13 Claims, 19 Drawing Sheets

(51) Int. Cl.
*A61B 1/04* (2006.01)
*H04N 5/225* (2006.01)
*H04N 5/232* (2006.01)
*H04N 9/04* (2006.01)
*A61B 1/06* (2006.01)
*H04N 5/235* (2006.01)
*A61B 1/00* (2006.01)

(52) U.S. Cl.
CPC ............ *A61B 1/06* (2013.01); *H04N 5/225* (2013.01); *H04N 5/232* (2013.01); *H04N 5/2356* (2013.01); *H04N 5/23229* (2013.01); *H04N 9/04* (2013.01); *A61B 1/0646* (2013.01); *H04N 5/2256* (2013.01); *H04N 2005/2255* (2013.01)

(58) Field of Classification Search
CPC ...... H04N 5/23229; H04N 9/04; H04N 5/232; H04N 5/225; H04N 2005/2255; H04N 5/2256
USPC .......................................................... 348/68
See application file for complete search history.

(56) References Cited

U.S. PATENT DOCUMENTS

| | | | |
|---|---|---|---|
| 2002/0126204 A1* | 9/2002 | Takeshige | A61B 1/00009 348/74 |
| 2003/0103212 A1* | 6/2003 | Westphal | A61B 3/102 356/479 |
| 2006/0257048 A1* | 11/2006 | Lin | G06K 9/00711 382/276 |
| 2014/0092227 A1* | 4/2014 | Kanamori | G01J 1/0209 348/68 |
| 2014/0362200 A1* | 12/2014 | Kanamori | A61B 1/0638 348/70 |
| 2015/0332473 A1 | 11/2015 | Cao | |
| 2018/0020932 A1* | 1/2018 | Chen | A61B 5/0261 600/479 |

OTHER PUBLICATIONS

Liu et al, Global-backgroud based view synthesis approach for multiview video (Year: 2012).*

International Search Report (ISR) and Written Opinion dated Jan. 27, 2015 issued in International Application No. PCT/JP2014/078974.

* cited by examiner

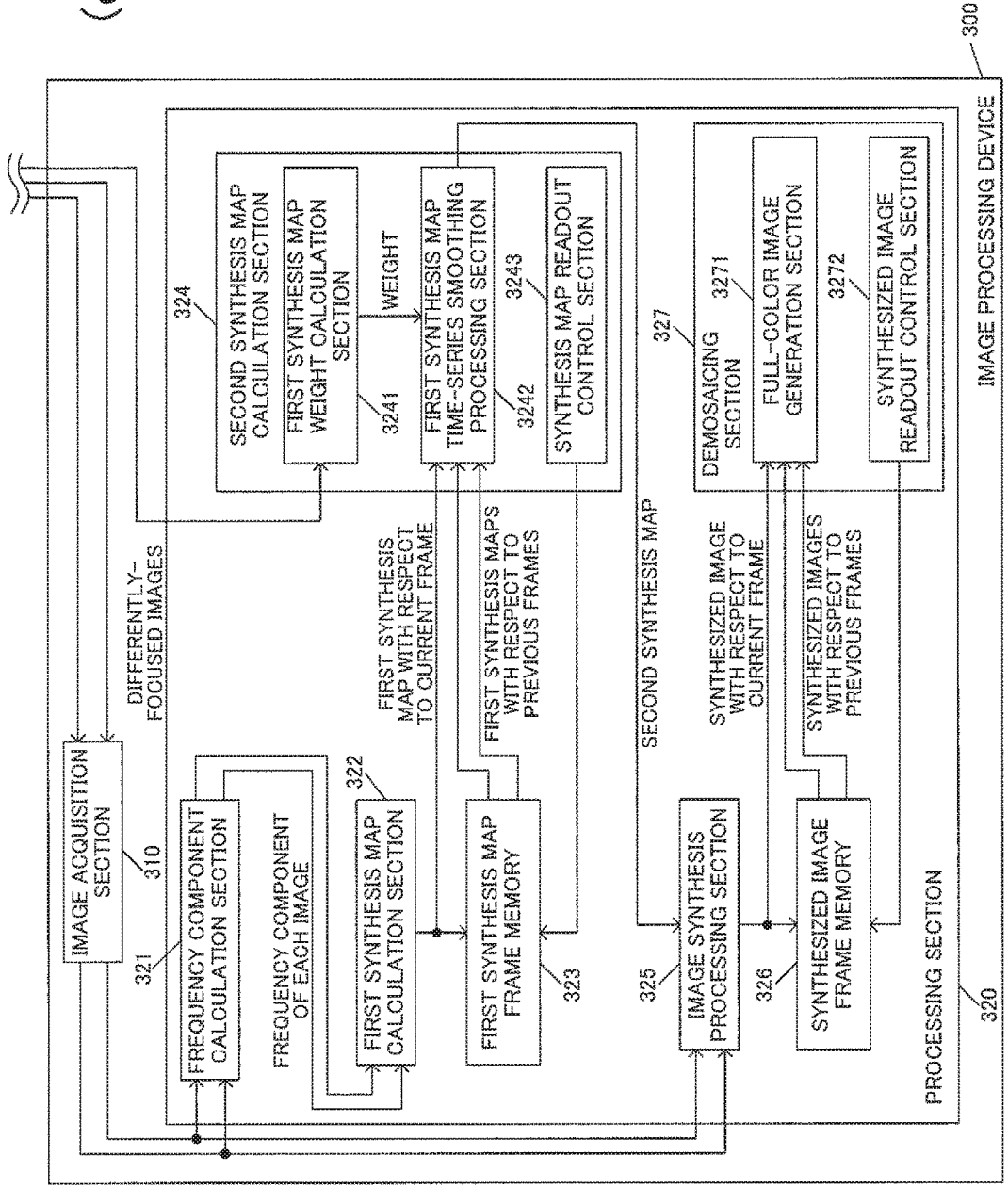
FIG.1 (con't)

| label | W0 | W1 | W2 |
|---|---|---|---|
| 0(R) | 0(R) | 0.5(B) | 0.5(G) |
| 1(G) | 0.5(G) | 0(R) | 0.5(B) |
| 2(B) | 0.5(B) | 0.5(G) | 0(R) |

FIG. 12

| label | C0 | C1 | C2 | C0*W0 | C1*W1 | C2*W2 |
|---|---|---|---|---|---|---|
| 0(R) | 0(R) | 2(B) | 0(G) | 0(R) | 1(B) | 0(G) |
| 1(G) | 2(G) | 0(R) | 0(B) | 1(G) | 0(R) | 0(B) |
| 2(B) | 2(B) | 0(G) | 0(R) | 1(B) | 0(G) | 0(R) |

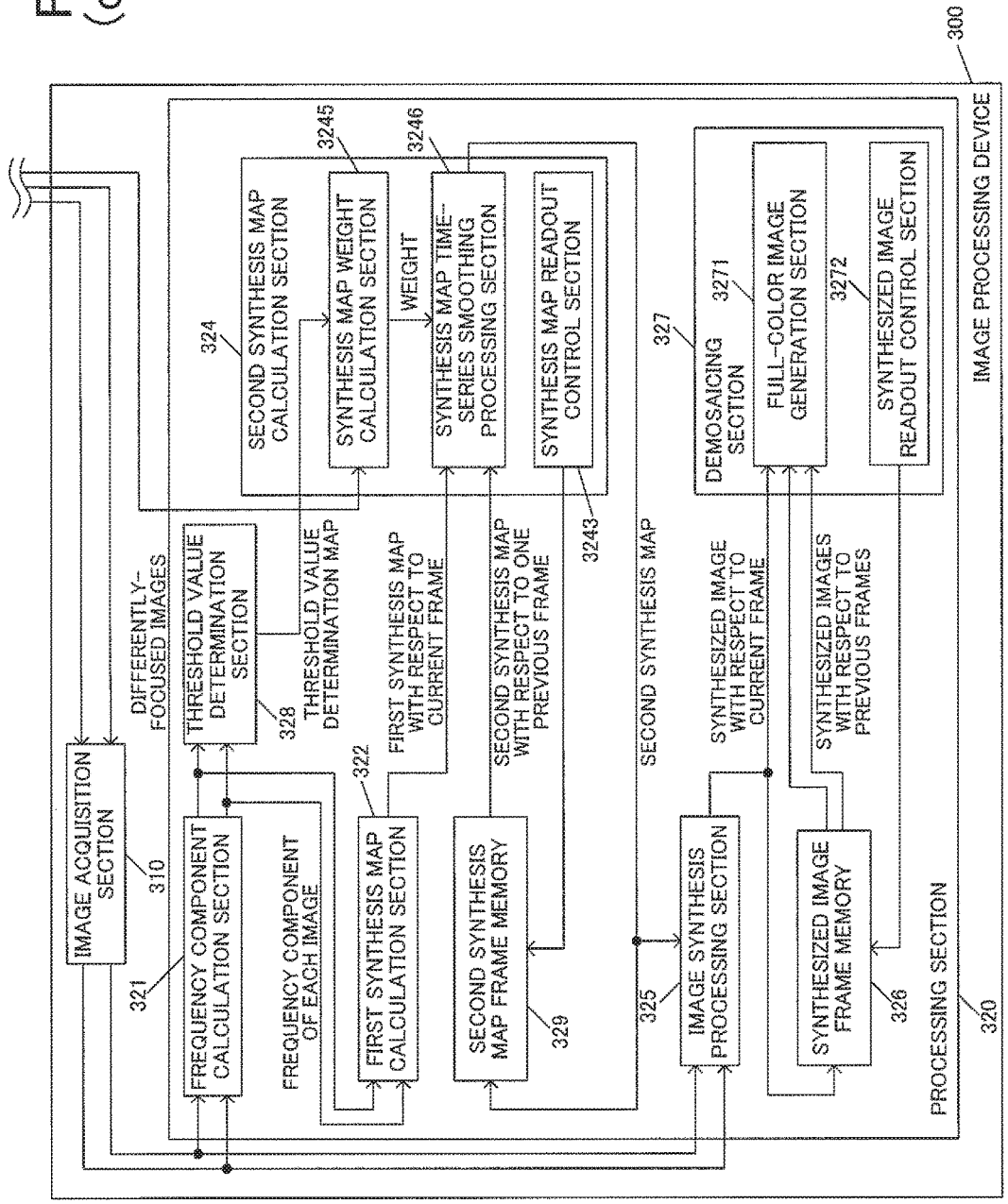

FIG. 15A

| label | W0 | W1 |
|---|---|---|
| 0(R) | 0(R) | 1(B) |
| 1(G) | 0(G) | 1(R) |
| 2(B) | 0(B) | 1(G) |

FIG. 15B

| label | W0 | W1 |
|---|---|---|
| 0(R) | 1(R) | 0(B) |
| 1(G) | 1(G) | 0(R) |
| 2(B) | 1(B) | 0(G) |

FIG. 15C

| label | W0 | W1 |
|---|---|---|
| 0(R) | 0(R) | 1(B) |
| 1(G) | 1(G) | 0(R) |
| 2(B) | 0.5(B) | 0.5(G) |

IMAGE PROCESSING DEVICE, ENDOSCOPE APPARATUS, AND IMAGE PROCESSING METHOD

CROSS REFERENCE TO RELATED APPLICATION

This application is a continuation of International Patent Application No. PCT/JP2014/078974, having an international filing date of Oct. 30, 2014, which designated the United States, the entirety of which is incorporated herein by reference.

BACKGROUND

The present invention relates to an image processing device, an endoscope apparatus, an image processing method, and the like.

A plurality of images that differ in focus state (hereinafter may be referred to as "differently-focused images") may be synthesized to generate an image in which a wide area (entire area in a narrow sense) is in focus (hereinafter may be referred to as "all-in-focus image"). The focus state changes depending on the control state of the optical system (e.g., focus lens), and a plurality of differently-focused images differ from each other as to the in-focus object plane position that represents the position of the object that is in an in-focus state, for example.

For example, JP-A-2013-84152 discloses a method that calculates a focus position probability distribution (i.e., the probability distribution with respect to the focus position) corresponding to each pixel position, and generates a synthesized image (all-in-focus image) using an optimum focus position calculated based on the focus position probability distribution.

According to JP-A-2013-84152, the focus position is estimated on a pixel basis by calculating the intensity of the frequency component from the grayscale image of the captured image (i.e., brightness information) to generate the synthesized image.

SUMMARY

According to one aspect of the invention, there is provided an image processing device comprising:
 a processor comprising hardware,
 the processor being configured to implement:
 an image acquisition process that acquires captured images from an imaging section that performs a frame sequential imaging process in which one cycle includes first to N-th (wherein N is an integer equal to or larger than 2) frames; and
 a synthesis process that synthesizes the captured images based on a synthesis map,
 wherein the processor implements the image acquisition process that acquires a plurality of the captured images that have been captured by the imaging section in an i-th (wherein i is an integer that satisfies $1 \leq i \leq N$) frame and differ from each other as to an in-focus object plane position, and
 the processor implements the synthesis process that calculates a first synthesis map based on the plurality of captured images that have been captured in the i-th frame and differ from each other as to the in-focus object plane position, calculates a second synthesis map based on the first synthesis map calculated with respect to the i-th frame, and the first synthesis map calculated with respect to a k-th (wherein k is an integer that satisfies $1 \leq k \leq N$ and $k \neq i$) frame that differs from the i-th frame, and synthesizes the plurality of images that have been captured in the i-th frame and differ from each other as to the in-focus object plane position based on the second synthesis map.

According to another aspect of the invention, there is provided an image processing device comprising:
 a processor comprising hardware,
 the processor being configured to implement:
 an image acquisition process that acquires captured images from an imaging section that performs a frame sequential imaging process in which one cycle includes first to N-th (wherein N is an integer equal to or larger than 3) frames that include at least an R frame, a G frame, and a B frame; and
 a synthesis process that synthesizes the captured images based on a synthesis map,
 wherein the processor implements the image acquisition process that acquires a plurality of the captured images that have been captured by the imaging section in an i-th (wherein i is an integer that satisfies $1 \leq i \leq N$) frame and differ from each other as to an in-focus object plane position, and
 the processor implements the synthesis process that calculates the synthesis map with respect to the i-th frame that corresponds to R based on the synthesis map calculated with respect to a frame that corresponds to G and the synthesis map calculated with respect to a frame that corresponds to B when the i-th frame is a frame that corresponds to R, and synthesizes the plurality of images that have been captured in the i-th frame and differ from each other as to the in-focus object plane position, based on the synthesis map.

According to another aspect of the invention, there is provided an endoscope apparatus comprising:
 the above image processing device; and
 the imaging section.

According to another aspect of the invention, there is provided an image processing method comprising:
 acquiring a plurality of captured images from an imaging section that performs a frame sequential imaging process in which one cycle includes first to N-th (wherein N is an integer equal to or larger than 2) frames, the plurality of captured images having been captured in an i-th (wherein i is an integer that satisfies $1 \leq i \leq N$) frame and differing from each other as to an in-focus object plane position;
 calculating a first synthesis map based on the plurality of captured images that have been captured in the i-th frame and differ from each other as to the in-focus object plane position;
 calculating a second synthesis map based on the first synthesis map calculated with respect to the i-th frame, and the first synthesis map calculated with respect to a k-th (wherein k is an integer that satisfies $1 \leq k \leq N$ and $k \neq i$) frame that differs from the i-th frame; and
 performing a synthesis process that synthesizes the plurality of captured images that have been captured in the i-th frame and differ from each other as to the in-focus object plane position based on the second synthesis map.

According to another aspect of the invention, there is provided an image processing method comprising:
 acquiring a plurality of captured images from an imaging section that performs a frame sequential imaging process in which one cycle includes first to N-th (wherein N is an integer equal to or larger than 3) frames that include at least an R frame, a G frame, and a B frame, the plurality of captured images having been captured in an i-th (wherein i is an integer that satisfies $1 \leq i \leq N$) frame and differing from each other as to an in-focus object plane position;

calculating a synthesis map with respect to the i-th frame that corresponds to R based on the synthesis map calculated with respect to a frame that corresponds to G and the synthesis map calculated with respect to a frame that corresponds to B when the i-th frame is a frame that corresponds to R; and performing a synthesis process that synthesizes the plurality of images that have been captured in the i-th frame and differ from each other as to the in-focus object plane position, based on the synthesis map.

BRIEF DESCRIPTION OF THE DRAWINGS

FIG. 12 illustrates another example of weight information that is used to generate a second synthesis map.

FIGS. 15A to 15C illustrate still another example of weight information that is used to generate a second synthesis map.

DESCRIPTION OF EXEMPLARY EMBODIMENTS

Figure 1:
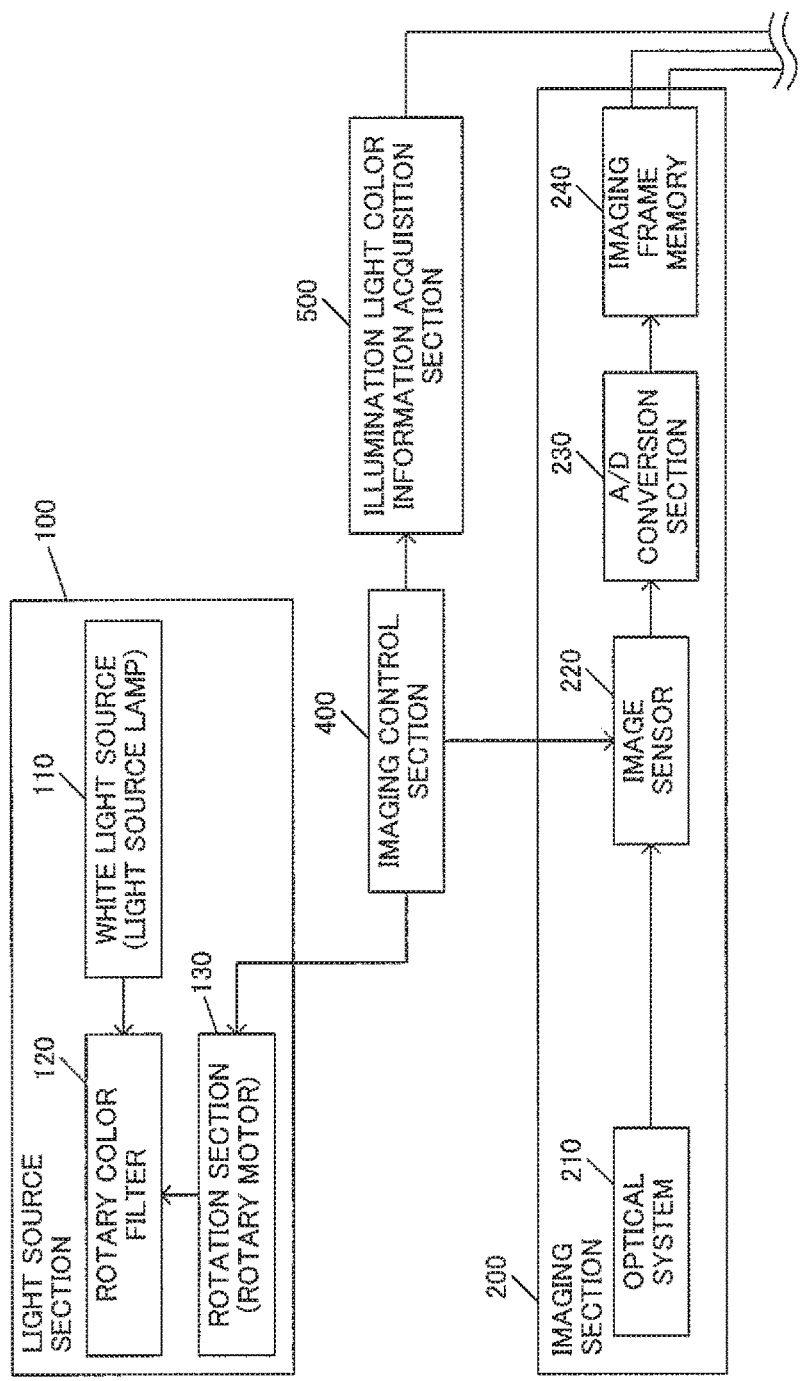
FIG. 1 illustrates a configuration example of an endoscope apparatus that includes an image processing device according to the embodiments of the invention.

According to one embodiment of the invention, there is provided an image processing device comprising:
a processor comprising hardware,
the processor being configured to implement:
an image acquisition process that acquires captured images from an imaging section that performs a frame sequential imaging process in which one cycle includes first to N-th (wherein N is an integer equal to or larger than 2) frames; and
a synthesis process that synthesizes the captured images based on a synthesis map,
wherein the processor implements the image acquisition process that acquires a plurality of the captured images that have been captured by the imaging section in an i-th (wherein i is an integer that satisfies 1≤i≤N) frame and differ from each other as to an in-focus object plane position, and the processor implements the synthesis process that calculates a first synthesis map based on the plurality of captured images that have been captured in the i-th frame and differ from each other as to the in-focus object plane position, calculates a second synthesis map based on the first synthesis map calculated with respect to the i-th frame, and the first synthesis map calculated with respect to a k-th (wherein k is an integer that satisfies 1≤k≤N and k≠i) frame that differs from the i-th frame, and synthesizes the plurality of images that have been captured in the i-th frame and differ from each other as to the in-focus object plane position based on the second synthesis map.

According to another embodiment of the invention, there is provided an image processing device comprising:
a processor comprising hardware,
the processor being configured to implement:
an image acquisition process that acquires captured images from an imaging section that performs a frame sequential imaging process in which one cycle includes first to N-th (wherein N is an integer equal to or larger than 3) frames that include at least an R frame, a G frame, and a B frame; and
a synthesis process that synthesizes the captured images based on a synthesis map,
wherein the processor implements the image acquisition process that acquires a plurality of the captured images that have been captured by the imaging section in an i-th (wherein i is an integer that satisfies 1≤i≤N) frame and differ from each other as to an in-focus object plane position, and the processor implements the synthesis process that calculates the synthesis map with respect to the i-th frame that corresponds to R based on the synthesis map calculated with respect to a frame that corresponds to G and the synthesis map calculated with respect to a frame that corresponds to B when the i-th frame is a frame that corresponds to R, and synthesizes the plurality of images that have been captured in the i-th frame and differ from each other as to the in-focus object plane position, based on the synthesis map.

According to another embodiment of the invention, there is provided an endoscope apparatus comprising:
the above image processing device; and
the imaging section.

According to another embodiment of the invention, there is provided an image processing method comprising:
acquiring a plurality of captured images from an imaging section that performs a frame sequential imaging process in which one cycle includes first to N-th (wherein N is an integer equal to or larger than 2) frames, the plurality of captured images having been captured in an i-th (wherein i is an integer that satisfies 1≤i≤N) frame and differing from each other as to an in-focus object plane position;

calculating a first synthesis map based on the plurality of captured images that have been captured in the i-th frame and differ from each other as to the in-focus object plane position;

calculating a second synthesis map based on the first synthesis map calculated with respect to the i-th frame, and the first synthesis map calculated with respect to a k-th (wherein k is an integer that satisfies 1≤k≤N and k≠i) frame that differs from the i-th frame; and performing a synthesis process that synthesizes the plurality of captured images that have been captured in the i-th frame and differ from each other as to the in-focus object plane position based on the second synthesis map.

According to another embodiment of the invention, there is provided an image processing method comprising:

acquiring a plurality of captured images from an imaging section that performs a frame sequential imaging process in which one cycle includes first to N-th (wherein N is an integer equal to or larger than 3) frames that include at least an R frame, a G frame, and a B frame, the plurality of captured images having been captured in an i-th (wherein i is an integer that satisfies 1≤i≤N) frame and differing from each other as to an in-focus object plane position;

calculating a synthesis map with respect to the i-th frame that corresponds to R based on the synthesis map calculated with respect to a frame that corresponds to G and the synthesis map calculated with respect to a frame that corresponds to B when the i-th frame is a frame that corresponds to R; and performing a synthesis process that synthesizes the plurality of images that have been captured in the i-th frame and differ from each other as to the in-focus object plane position, based on the synthesis map.

The exemplary embodiments of the invention are described below. Note that the exemplary embodiments described below do not in any way limit the scope of the invention laid out in the claims. Note also that all of the elements described below in connection with the exemplary embodiments should not necessarily be taken as essential elements of the invention.

1. Method

A method used in connection with the exemplary embodiments of the invention is described below. In recent years, a method that synthesizes a plurality of differently-focused images to generate an all-in-focus image (all-focused image) has been used. For example, a first image in which a position situated at a short distance from the imaging section is in focus, and a second image in which a position situated at a long distance from the imaging section is in focus (as compared with the first image), are acquired as a plurality of differently-focused images. The expression "a position situated at a short distance from the imaging section is in focus" may be interpreted to mean that the in-focus object plane position is situated close to the imaging section. The first image and the second image are basically identical to each other as to the angle of view (i.e., object capture range).

In such a case, it is considered that a first object (captured object) that is situated at a relatively short distance from the imaging section is in focus within the first image, and a second object (captured object) that is situated at a relatively long distance from the imaging section is in focus within the second image. Therefore, when a synthesized image is generated by employing the pixel values of the first image with respect to an area in which the first object is captured, and employing the pixel values of the second image with respect to an area in which the second object is captured, the first object and the second object are in focus within the synthesized image.

Specifically, whether the first image or the second image is in better focus may be determined with respect to each pixel (or an area that includes a plurality of pixels) of the captured image, and the determination process may be performed using an evaluation value (e.g., contrast). It is determined that the first image is in better focus with respect to the processing target pixel when the evaluation value obtained from the first image is larger than the evaluation value obtained from the second image, and it is determined that the second image is in better focus with respect to the processing target pixel when the evaluation value obtained from the first image is equal to or smaller than the evaluation value obtained from the second image. When the difference in evaluation value is small, the pixel value of the first image and the pixel value of the second image may be synthesized to calculate the pixel value of the processing target pixel within the synthesized image.

Although an example in which two differently-focused images are used has been described above, three or more differently-focused images may be used. In principle, an object that is in focus within one of a plurality of differently-focused images can be brought into focus within the synthesized image (see above). Therefore, it is possible to bring an object that is distributed over a wide distance range into focus, or bring a wide area within the captured image into focus, by increasing the number of differently-focused images, for example.

Note that the in-focus distance range within each differently-focused image differs depending on the in-focus object plane position and the depth of field, and the object distribution distance range varies depending on the object and the imaging conditions. Therefore, even when the number of differently-focused images is small, it may be possible to acquire a synthesized image in which a wide area is in focus depending on various conditions. Note that there is a tendency that it is basically possible to acquire a synthesized image in which the object is in focus over a wide distance range as the number of differently-focused images increases.

For example, a method that synthesizes several tens of differently-focused images in real time has been used in recent years in the fields of a microscope and the like. In this case, the synthesized image is also referred to as "all-in-focus image" since it is considered that an image in which the entire field of view (entire captured image) is in focus can be output. An image that is to be subjected to the synthesis process may be hereinafter referred to as "differently-focused image", and an image that has been obtained by the synthesis process may be hereinafter referred to as "all-in-focus image". Note that the term "all-in-focus image" does not necessarily mean that the entire area within the image (entire image) is in focus.

A frame sequential method is known as an imaging method. The frame sequential method may be implemented using the light source section 100 illustrated in FIG. 1, for example. The light source section 100 includes a white light source 110, a rotary color filter 120 that has a plurality of spectral transmittances, and a rotation section 130 that drives the rotary color filter 120. As illustrated in FIG. 2, the rotary color filter 120 includes a red (R) filter 121, a green (G) filter 122, and a blue (B) filter 123, for example. The elements illustrated in FIG. 1 other than the light source section 100 are described later.

The rotation section 103 rotates the rotary color filter 120 at a given rotational speed in synchronization with the imaging period of an image sensor 220 based on a control signal output from an imaging control section 400. For example, when the color filter is rotated at 20 revolutions per second, each color filter crosses the incident white light every $\frac{1}{60}$th of a second, and the image sensor 220 captures the reflected light (R, G, or B) from the observation target, and transfers the resulting image every $\frac{1}{60}$th of a second. Specifically, an R image, a G image, and a B image are captured every $\frac{1}{60}$th of a second, and the substantial frame rate is 20 fps.

Figure 3A:
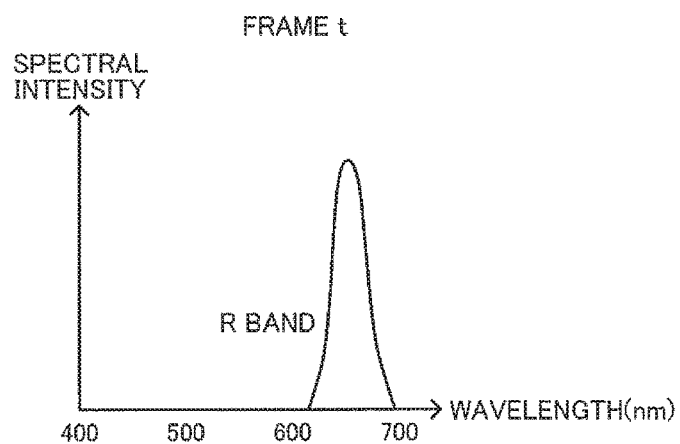
FIGS. 3A to 3C illustrate an example of the spectral characteristics of each filter, and a frame.
Figure 3B:
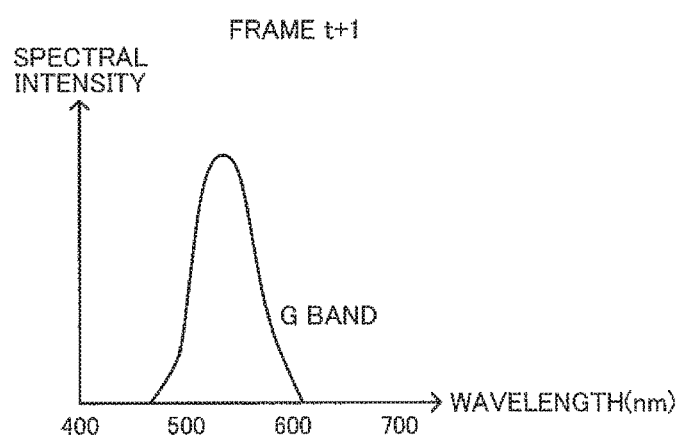
Figure 3C:
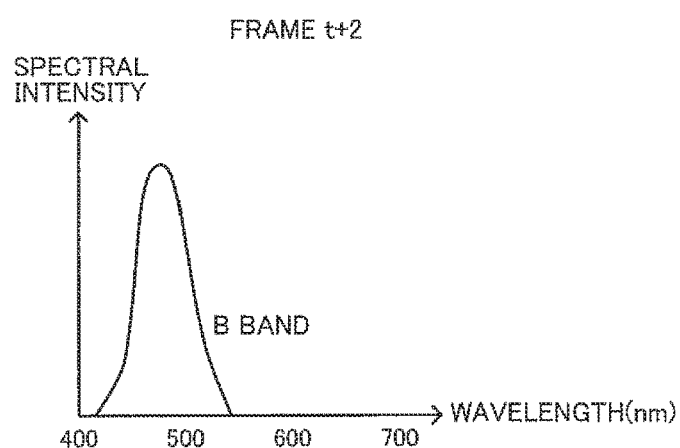

FIGS. 3A to 3C illustrate the spectral characteristics of the filters 121 to 123. In the example illustrated in FIGS. 3A to 3C, R-band light that has passed through the filter 121 is applied in a given frame t, G-band light that has passed through the filter 122 is applied in a frame t+1 that follows the frame t, and B-band light that has passed through the filter 123 is applied in a frame t+2 that follows the frame t+1.

When the frame sequential method is used, a signal that corresponds to one color (one channel or wavelength band) is acquired in a given frame with respect to each pixel of the image sensor. When a Bayer array image sensor is used, an R signal, a G signal, and a B signal are acquired in a given frame with respect to only pixels that account for a quarter or half of the total number of pixels of the image sensor. Therefore, it is necessary to perform an interpolation process for acquiring an R signal, a G signal, and a B signal on a pixel basis when a Bayer array image sensor or the like is used, and a decrease in resolution occurs. Specifically, the frame sequential method is advantageous over a method that uses a Bayer array image sensor or the like in terms of resolution since a signal that corresponds to each channel can be acquired with respect to each pixel of the image sensor. However, since only a signal that corresponds to one color can be acquired in each frame, it is necessary to synthesize signals acquired in a plurality of frames in order to output a color image in which each color is synthesized. For example, when R, G, and B are used, one color image is output per three frames, and the frame rate is lower than that achieved when a Bayer array image sensor or the like is used.

The method that synthesizes a plurality of differently-focused images to generate an all-in-focus image, and the frame sequential imaging method have been used as described above. However, it was found that a problem occurs when these methods are used in combination.

Figure 4:
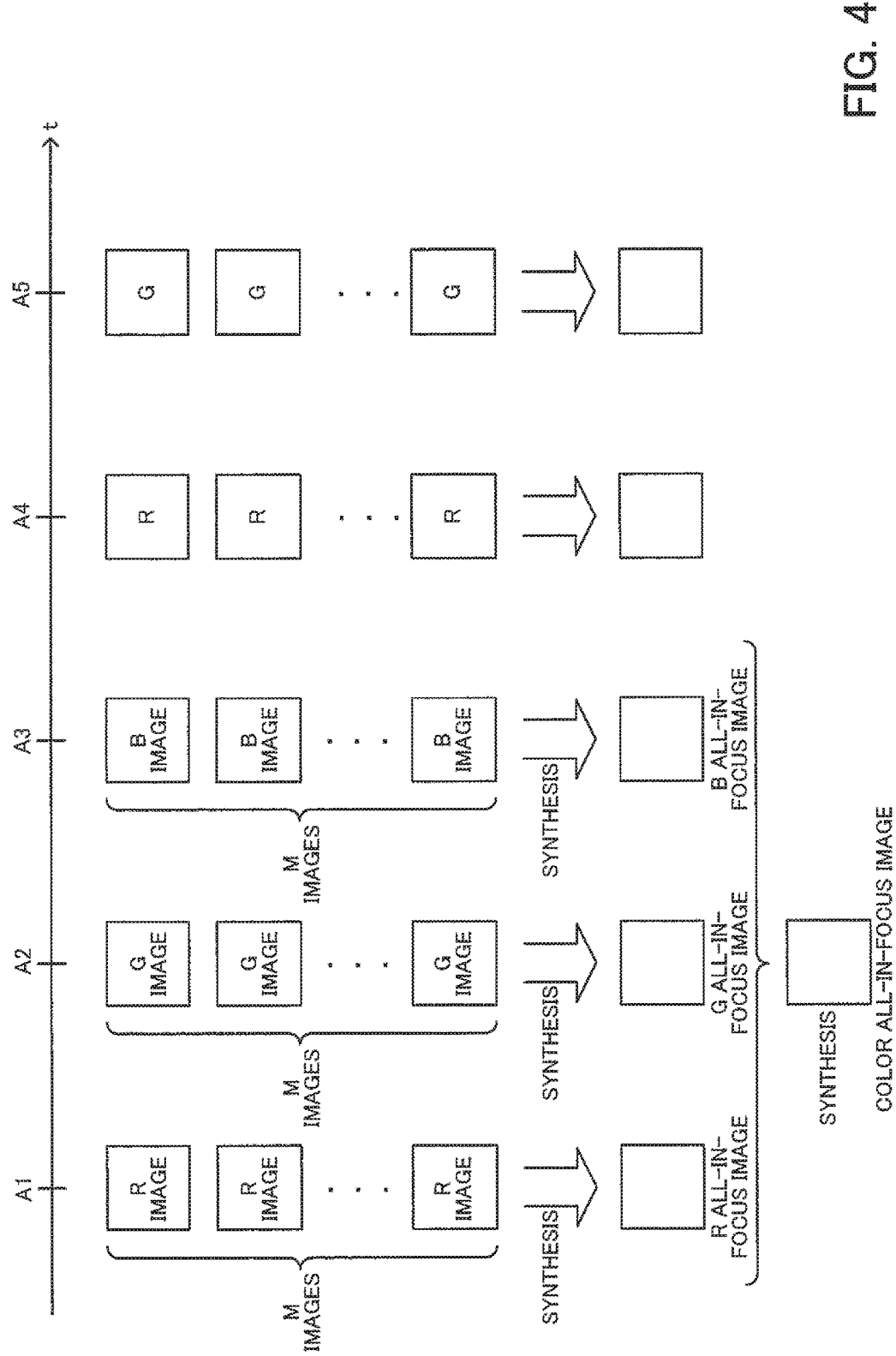
FIG. 4 is a view illustrating a method according to the embodiments of the invention.

A specific combination example is described below with reference to FIG. 4. Although FIG. 4 illustrates an example in which R, G, and B are used, the number of channels (i.e., the number of frames required to output one color image) may be arbitrarily set as long as the number of channels is equal to or larger than 2. In FIG. 4, the horizontal axis indicates time. A plurality of differently-focused images are acquired in a given frame using a signal that corresponds to a specific color. For example, M (M is an integer equal to or larger than 2) R images that differ from each other as to the in-focus object plane position are acquired in the frame A1 illustrated in FIG. 4. Likewise, M G images are acquired in the frame A2, and M B images are acquired in the frame A3.

A plurality of (M) differently-focused images are synthesized on a frame basis to generate an all-in-focus image that corresponds to each specific color signal. Specifically, the M R images acquired in the frame A1 are synthesized to generate an R all-in-focus image, the M G images acquired in the frame A2 are synthesized to generate a G all-in-focus image, and the M B images acquired in the frame A3 are synthesized to generate a B all-in-focus image. Each all-in-focus image includes a monochromatic signal (see above). The R all-in-focus image, the G all-in-focus image, and the B all-in-focus image are synthesized to output one color image. The above process is repeated with respect to the subsequent frames to output one all-in-focus image per three frames.

According to the known technology described above, the focus position is estimated on a pixel basis by calculating the intensity of the frequency component from the grayscale image of the captured image (i.e., brightness information) to generate a synthesized image. In the example illustrated in FIG. 4, the process is performed using the M R images when generating the R all-in-focus image, is performed using the M G images when generating the G all-in-focus image, and is performed using the M B images when generating the B all-in-focus image.

However, when the wavelength band of the color that forms the contrast with respect to the contour or the texture of the object does not overlap the wavelength band of the illumination light, the intensity of the frequency component that is calculated described above is low, and the effect of noise relatively increases. As a result, the focus position estimation accuracy decreases, whereby the image synthesis accuracy decreases. In particular, since the wavelength of the illumination light to be applied differs on a frame basis when the frame sequential imaging method is used, the image synthesis accuracy also differs on a frame basis.

For example, when a tissue image is captured using an endoscope for which the frame sequential imaging method is widely used, there is a tendency that the intensity of the frequency component decreases within an image captured using R-channel illumination light. For example, a blood vessel serves as an element that forms contrast within an image. The color of a blood vessel is mainly formed by a G signal and a B signal, and an R signal contributes to only a small extent to the color of a blood vessel. Therefore, a blood vessel forms high contrast within a G image and a B image, but forms very low contrast within an R image. As a result, a defocus state occurs with respect to only an R-channel image during the demosaicing process that is performed when the frame sequential imaging method is used, and the RGB balance (i.e., color) of a blood vessel or the like is impaired.

Figures 5, 6:
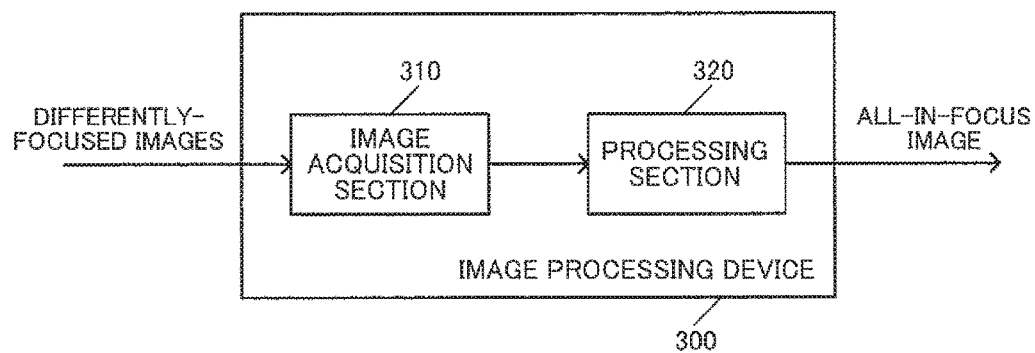
FIG. 5 illustrates a configuration example of an image processing device according to the embodiments of the invention.
FIG. 6 illustrates an example of weight information that is used to generate a second synthesis map.

In order to deal with the above problem, the invention proposes a method that synthesizes a plurality of differently-focused images captured in a given frame optionally using information obtained in another frame. As illustrated in FIG. 5, an image processing device 300 according to the exemplary embodiments of invention includes an image acquisition section 310 that acquires captured images from an imaging section 200 that performs a frame sequential imaging process in which one cycle includes first to N-th (wherein N is an integer equal to or larger than 2) frames, and a processing section 320 that performs a synthesis process that synthesizes the captured images based on a synthesis map.

The image acquisition section 310 acquires a plurality of captured images that have been captured by the imaging section 200 in an i-th (wherein i is an integer that satisfies 1≤i≤N) frame and differ from each other as to the in-focus object plane position. This process corresponds to a process that acquires M differently-focused images that correspond to each color (wavelength band) in each frame (see above).

The processing section 320 calculates a first synthesis map based on the plurality of captured images that have been captured in the i-th frame and differ from each other as to the in-focus object plane position, and calculates a second synthesis map based on the first synthesis map calculated with respect to the i-th frame, and a first synthesis map calculated with respect to a k-th (wherein k is an integer that satisfies 1≤k≤N and k≠i) frame that differs from the i-th frame. The processing section 320 synthesizes the plurality of captured images that have been captured in the i-th frame and differ from each other as to the in-focus object plane position based on the second synthesis map.

The term "synthesis map" used herein refers to information (synthesis information) that is used for the synthesis process that synthesizes a plurality of differently-focused images. For example, the synthesis map may be information in which information that determines the pixel value of each pixel is linked to each pixel of an image. The information that determines the pixel value of each pixel is not particularly limited. When the pixel values of a given differently-focused image are directly used as the pixel values of the all-in-focus image, the information that determines the pixel value of each pixel is information (e.g., image ID information) that specifies the selection target differently-focused image. When the pixel values of a plurality of differently-focused images are synthesized to calculate the pixel values of the all-in-focus image, information that represents the synthesis ratio may be used as the information that determines the pixel value of each pixel.

The first synthesis map with respect to the i-th frame is calculated from a plurality of differently-focused images acquired in the i-th frame. Specifically, the first synthesis map is a synthesis map that is calculated from information obtained from a given frame.

On the other hand, the second synthesis map is a synthesis map that is used for the synthesis process. Specifically, when synthesizing a plurality of differently-focused images acquired in a given frame, it is possible to utilize information acquired from another frame in addition to the information acquired from the given frame. Therefore, even when it is impossible to perform an accurate synthesis process using only the information acquired from the given frame, it is possible to perform an accurate synthesis process on the differently-focused images captured in the given frame since information acquired from another frame can be used.

For example, when the synthesis process is performed on an object that has low contrast with respect to an R signal (e.g., a blood vessel captured within an in vivo image), since the accuracy of the first synthesis map calculated from the R signal is low, the synthesis accuracy with respect to the R all-in-focus image decreases when the synthesis process is performed based on the first synthesis map calculated from the R signal. However, since the method according to the exemplary embodiments of the invention can synthesize a plurality of R differently-focused image using the first synthesis map calculated from the G signal or the first synthesis map calculated from the B signal, for example, it is possible to accurately calculate the R all-in-focus image.

A first embodiment, a second embodiment, and a third embodiment of the invention are described below. A basic method will be described in connection with the first embodiment, and a timeseries weighting method used when calculating the second synthesis map will be described in connection with the second embodiment. A method that selectively uses a plurality of types of weighting using an evaluation value, and a method that uses the second synthesis map calculated in advance for a process performed with respect to a different frame, will be described in connection with the third embodiment.

2. First Embodiment

Figure 2:
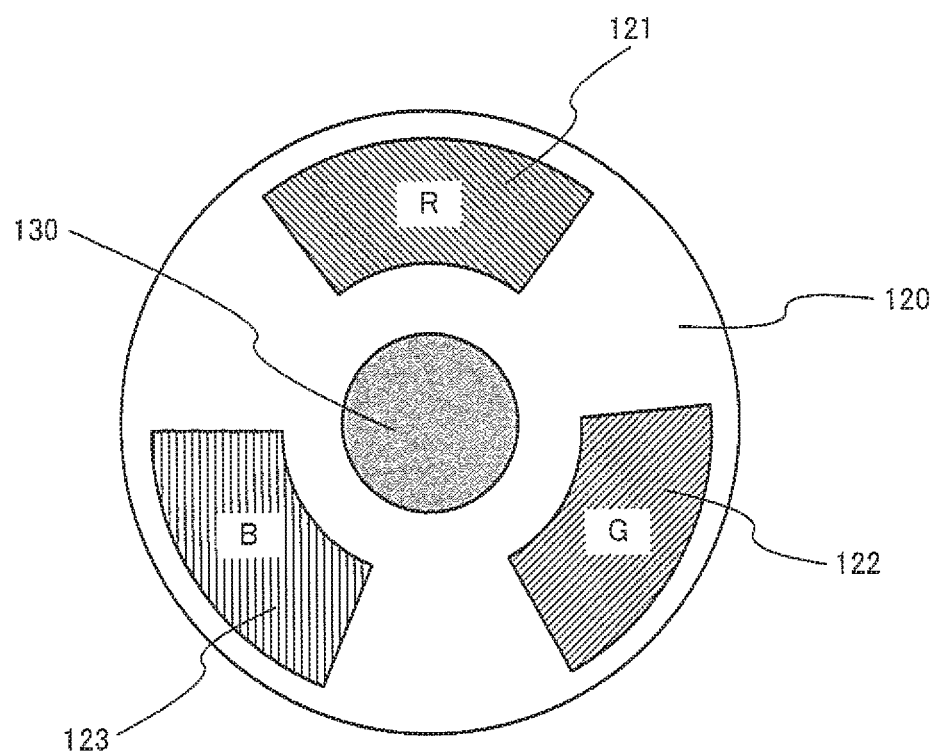
FIG. 2 illustrates a configuration example of a rotary color filter.

FIG. 1 illustrates a system configuration example of an image processing device 300 according to the first embodiment, and an endoscope apparatus (electronic device in a broad sense) that includes the image processing device 300. As illustrated in FIG. 1, the endoscope apparatus includes a light source section 100, an imaging section 200, the image processing device 300, an imaging control section 400, and an illumination light color information acquisition section 500. Note that the image processing device 300 and the endoscope apparatus are not limited to the configuration illustrated in FIG. 1. Various modifications and variations may be made, such as omitting some of the elements illustrated in FIG. 1, or providing an additional element. Although FIG. 1 illustrates an example in which the imaging control section 400 and the illumination light color information acquisition section 500 are provided separately from the image processing device 300, the image processing device 300 may include the imaging control section 400 and the illumination light color information acquisition section 500.

The light source section 100 includes a white light source (light source lamp) 110, a rotary color filter 120, and a rotation section 130 (rotary motor). The light source section 100 is configured in the same manner as described above, and detailed description thereof is omitted. Note that the rotary color filter 120 illustrated in FIG. 2 includes the filters 121 to 123 that differ in spectral characteristics since R, G, and B are used. The rotary color filter 120 includes N filters when N wavelength bands are used. Although an example in which R, G, and B are used is described below, the following description may be similarly applied to the case where the number N of colors is other than 3.

The imaging section 200 includes an optical system (lens system) 210, an image sensor 220, an A/D conversion section 230, and an imaging frame memory 240. The optical system 210 may be configured in various ways. For example, the optical system 210 may include a zoom lens and a focus lens. The image sensor 220 receives reflected light through the optical system 210, the reflected light being light within a specific wavelength band that has passed through the rotary color filter 120 and has been reflected by the object. The image sensor 220 acquires a signal within the specific wavelength band over the entirety (i.e., each pixel) of the image sensor 220.

The A/D conversion section 230 converts the analog signal output from the image sensor 220 into a digital signal. The imaging frame memory 240 is a memory that stores the captured image that has been subjected to the A/D conversion process.

The optical system 210 and the image sensor 220 are configured so that M images that differ from each other as to the in-focus object plane position (focus position) can be acquired at the same time with respect to the same object. Specifically, a stereo camera may be used, and the imaging section 200 may include M optical systems 210 and M image sensors 220. Alternatively, the incident light may be divided (split) using a prism or the like. In this case, the optical system 210 may include only one lens, but needs to include a prism and a half mirror for dividing the incident light into M parts, and M image sensors 220 are used corresponding to each divided light. Although an example in which two differently-focused images are acquired is described below for convenience of explanation, the following description can similarly be applied to the case where three or more differently-focused images are acquired.

The imaging control section 400 synchronizes a control process that controls the rotation section 130 that rotates the rotary color filter 120 provided in front of the white light source 110, and a readout control process that is performed on the image sensor 220, and stores an image captured using the frame sequential method in the imaging frame memory 240.

The illumination light color information acquisition section 500 acquires a label based on a signal output from the imaging control section 400, the label representing the color (R, G, or B) of light applied in each frame. For example, the label is set to "0" when the color of light is "R", is set to "1" when the color of light is "G", and is set to "2" when the color of light is "B".

The image processing device 300 includes the image acquisition section 310 and the processing section 320 (see above). The image acquisition section 310 acquires the captured images that have been captured by the imaging section 200. The captured images that are acquired by the image acquisition section 310 are a plurality of images (i.e., a plurality of differently-focused images) that are to be subjected to the synthesis process. The image acquisition section 310 may be implemented by an interface that interfaces between the image processing device 300 and the imaging section 200, for example. The image acquisition section 310 may include a memory that stores the captured image.

The processing section 320 performs a process that synthesizes a plurality of differently-focused images to calculate (generate) an all-in-focus image, and the like. The function of the processing section 320 may be implemented by hardware such as a processor (e.g., CPU) or an ASIC (e.g., gate array), a program, or the like.

The processing section 320 includes a frequency component calculation section 321, a first synthesis map calculation section 322, a first synthesis map frame memory 323, a second synthesis map calculation section 324, an image synthesis processing section 325, a synthesized image frame memory 326, and a demosaicing section 327.

The details of each section included in the processing section 320, and the flow of the process according to the first embodiment, are described below. Although an example in which R, G, and B are used (N=3), and two differently-focused images are synthesized (M=2), is described below, various modifications and variations may be made with regard to the number M and the number N (see above).

The frequency component calculation section 321 calculates an evaluation value e using a given frequency band extraction filter with respect to each of the plurality of differently-focused images, and outputs the calculated evaluation value e. A common differential filter, or a band-pass filter for which the filter size and the coefficient have been calculated experimentally, may be used as the filter. The information calculated by the frequency component calculation section 321 is a contrast value used for a common contrast AF process, for example. The evaluation value e is the contrast value, or a value calculated based on the contrast value, for example. When M=2 (i.e., when two differently-focused images are synthesized), the frequency component calculation section 321 outputs two evaluation values e1(x) and e2(x) with respect to each image coordinate x. The evaluation value e1 is the evaluation value e calculated from the first differently-focused image (that corresponds to focus 1), and the evaluation value e2 is the evaluation value e calculated from the second differently-focused image (that corresponds to focus 2).

The first synthesis map calculation section 322 calculates a value MF using an evaluation value E(x) that represents the quantitative relationship between the evaluation value e1(x) and the evaluation value e2(x), and outputs the calculated value MF, the value MF representing whether to select the first differently-focused image or the second differently-focused image (for generating the synthesized image) on a coordinate basis. A set of the values MF that are calculated on a pixel basis and correspond to the entire image (i.e., the entire area within the image) represents a first synthesis map.

The ratio of the evaluation value e1(x) to the evaluation value e2(x), or the difference between the evaluation value e1(x) and the evaluation value e2(x), may be used as the evaluation value E. The value MF may be calculated by the following expression (1) using the evaluation value E, for example. Note that E1 and E2 are threshold values that are calculated experimentally, "1" means that the image that corresponds to focus 1 is synthesized in a ratio of 100%, and "0" means that the image that corresponds to focus 2 is synthesized in a ratio of 100%.

$$MF(x) = \begin{cases} 1 & E(x) \geq E2 \\ 0 & E(x) \leq E1 \\ \frac{E(x) - E1}{E2 - E1} & E1 < E(x) < E2 \end{cases} \quad (1)$$

The first synthesis map frame memory 323 stores the first synthesis map calculated as described above. The first synthesis map calculated with respect to the j-th previous frame based on the current frame is referred to as "MFj". The first synthesis map calculated with respect to the current frame is referred to as "MF0".

The second synthesis map calculation section 324 calculates the second synthesis map using the label of illumination light color information, the first synthesis map calculated with respect to the current frame, and the first synthesis map calculated with respect to the previous frame. More specifically, the second synthesis map calculation section 324 includes a first synthesis map weight calculation section (weight calculation section) 3241, a first synthesis map time-series smoothing processing section (weighted averaging processing section) 3242, and a synthesis map readout control section 3243.

The first synthesis map weight calculation section 3241 calculates a weight Wi(x) based on the label of the illumination light color information, the weight Wi(x) being used to perform a weighted averaging process on N first synthesis maps that correspond to the cycle of the frame sequential imaging process. The weight is set to satisfy the following expression (2).

$$\sum_{i=0}^{N-1} W_i(x) = 1 \quad (2)$$

When R, G, and B are used (N=3), the weights W0(x), W1(x), and W2(x) are calculated to satisfy the following expression (2). In the first embodiment, the label is set to "0" when the wavelength band of the illumination light is "R", set to "1" when the wavelength band of the illumination light is "G", and set to "2" when the wavelength band of the illumination light is "B". Therefore, the weight may be set as illustrated in FIG. 6 (table), for example. Note that FIG. 6 illustrates an example in which light is applied in the order R, G, B, R, . . . . Specifically, when the label is set to "0" (i.e., when the current frame is "R", the frame that immediately precedes the current frame is "B", and the frame that immediately precedes the frame that immediately precedes the current frame is "G"), W0 represents the weight that is calculated from the R signal and applied to the first synthesis map, W1 represents the weight that is calculated from the B signal and applied to the first synthesis map, and W2 represents the weight that is calculated from the G signal and applied to the first synthesis map. Likewise, when the label is set to "1" (i.e., when the current frame is "G"), W0 represents the weight that is calculated from the G signal, W1 represents the weight that is calculated from the R signal, and W2 represents the weight that is calculated from the B signal. When the label is set to "2" (i.e., when the current frame is "B"), W0 represents the weight that is calculated from the B signal, W1 represents the weight that is calculated from the G signal, and W2 represents the weight that is calculated from the R signal.

As illustrated in FIG. 6, the weight with respect to the frame in which light within the R wavelength band was applied is set to "0", and the weight with respect to the frame in which light within the G or B wavelength band was applied is set to "0.5". Note that the weight used when performing the weighted averaging process on the first synthesis maps to calculate the second synthesis map, is not limited thereto. For example, it is desirable to experimentally determine an optimum value with respect to the object with regard to the values included in the table illustrated in FIG. 6.

For example, when the contrast cannot be accurately calculated from the R signal (e.g., when the object is a blood vessel within an in vivo image), the weight that corresponds to the R signal is relatively decreased, and the weight that corresponds to the G signal, and the weight that corresponds to the B signal are relatively increased. Note that this process is not limited to R. When it is known that the accuracy decreases with respect to a specific channel among N channels, the weight that corresponds to the specific channel may be decreased, and the weight that corresponds to the remaining channel(s) may be increased. The weight need not necessarily be set to "0" when the weight is decreased. A value that is relatively small and is other then "0" may be used as the weight.

The synthesis map readout control section 3243 reads the first synthesis map MFi that has been stored with respect to the current frame and two previous frames. When one cycle includes three frames (R, G, and B), the synthesis map readout control section 3243 reads the first synthesis maps MF0, MF1, and MF2. When one cycle includes N frames, the synthesis map readout control section 3243 reads the first synthesis maps that correspond to N frames. Specifically, the synthesis map readout control section 3243 reads N first synthesis maps MF0 to MFN−1.

The first synthesis map time-series smoothing processing section 3242 calculates a second synthesis map MS that is used when synthesizing a plurality of differently-focused images captured in the current frame using the following expression (3), and outputs the second synthesis map MS.

$$MS(x) = \sum_{i=0}^{N-1} W_i(x) \times MF_i(x) \quad (3)$$

According to the process performed by the second synthesis map calculation section 324, the weight applied to the synthesis map calculated with respect to a frame in which the illumination light has a color that does not easily form the contrast of the object is decreased, and subjected to the weighted averaging process with the value of the synthesis map calculated with respect to each of the remaining frames. The second synthesis map calculated by the first synthesis map time-series smoothing processing section 3242 is output to the image synthesis processing section 325.

The image synthesis processing section 325 synthesizes the first differently-focused image and the second differently-focused image based on the second synthesis map calculated as described above, and stores the resulting synthesized image in the synthesized image frame memory 326. More specifically, when the pixel value of the synthesized image (all-in-focus image) at the pixel position x is referred to as "I'(x)", the pixel value of the first differently-focused image at the pixel position x is referred to as "I1(x)", and the pixel value of the second differently-focused image at the pixel position x is referred to as "I2(x)", the image synthesis processing section 325 performs the synthesis process using the following expression (4). As described above, only the pixel value of the first differently-focused image is used as the pixel value of the synthesized image at the pixel position x when MS(x)=1, and only the pixel value of the second differently-focused image is used as the pixel value of the synthesized image at the pixel position x when MS(x)=0.

$$I'(x) = MS(x) \times I1(x) + \{1 - MS(x)\} \times I2(x) \quad (4)$$

The above process is performed on the information that corresponds to one cycle (3 frames) to acquire an all-in-focus image that corresponds to each color. The demosaicing section 327 generates an RGB full-color image that corresponds to the current frame based on the synthesized images calculated with respect to one cycle of the frame sequential imaging process.

The demosaicing section 327 may include a full-color image generation section 3271 and a synthesized image readout control section 3272. The synthesized image readout control section 3272 reads the synthesized image stored in the synthesized image frame memory 326 with respect to the previous frame on condition that the frame is a given frame. In the example illustrated in FIG. 4, a color image is output using the information obtained from the frames A1 to A3. In this case, when the current frame is the frame A3 (B frame), the synthesized image readout control section 3272 reads the synthesized images stored corresponding to two previous frames (R and G frames).

The full-color image generation section 3271 performs a process that synthesizes the synthesized images that correspond to the previous frames and have been read as described above, and the synthesized image that corresponds to the current frame to generate a full-color image, and outputs the generated full-color image.

Figure 7A:
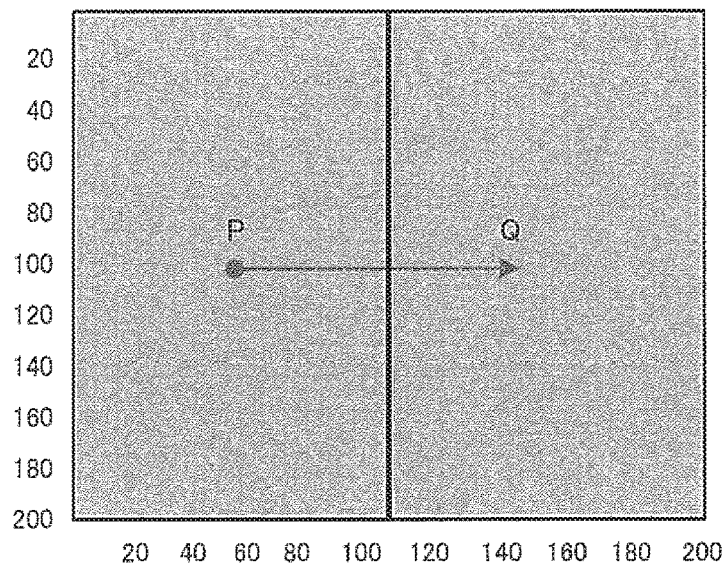
FIGS. 7A and 7B illustrate an example of differently-focused images.
Figure 7B:
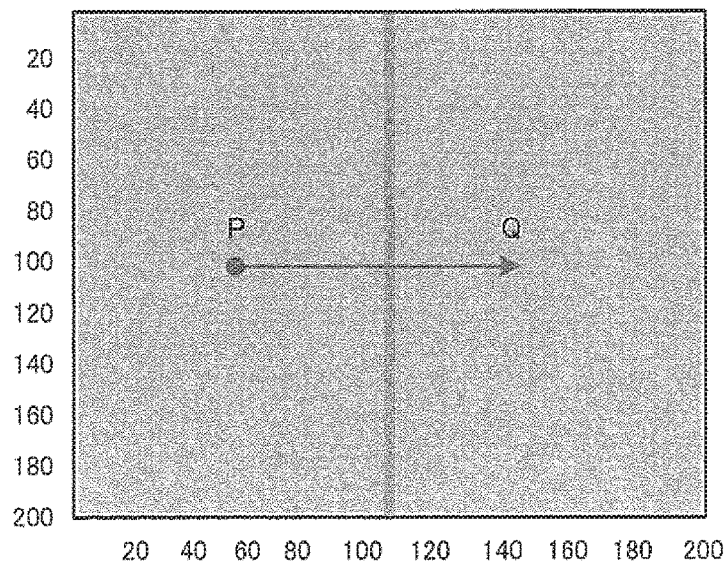

The advantageous effects achieved by the first embodiment are described below with reference to FIGS. 7A to 8F by means of a comparison with a known method. FIG. 7A illustrates an example of an image in a first focus state, and FIG. 7B illustrates an example of an image in a second focus state. FIGS. 7A and 7B are schematic views illustrating a full-color image. In the first embodiment, a monochromatic image that corresponds to the image illustrated in FIG. 7A is acquired in each frame (R, G, and B) as the first differently-focused image, and a monochromatic image that corresponds to the image illustrated in FIG. 7B is acquired in each frame (R, G, and B) as the second differently-focused image. The line that is observed in the center area of each image and extends in the vertical direction represents a blood vessel. While the blood vessel is clearly observed in FIG. 7A, the blood vessel is obscure in FIG. 7B. Specifically, a synthesized image in which the blood vessel is in focus can be obtained by setting the pixel values of the first differently-focused image to be the pixel values of the synthesized image at least in an area around the blood vessel with respect to each frame (R, G, and B).

Figure 8A:
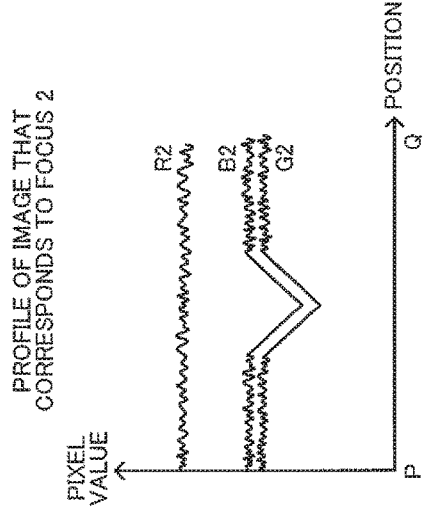
FIGS. 8A to 8F illustrate an example of a comparison between a method according to the embodiments of the invention and a known method.
Figure 8B:
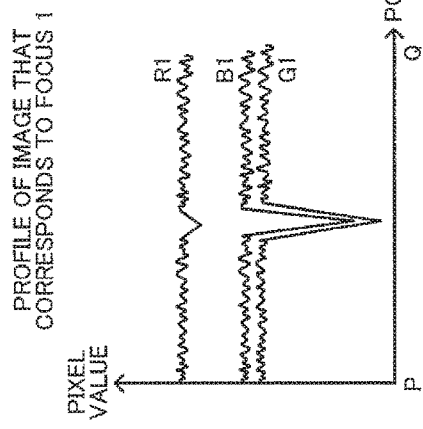

A point P and a point Q are set at given positions within the first differently-focused image and the second differently-focused image. The position of the point P within the first differently-focused image coincides with the position of the point P within the second differently-focused image, and the position of the point Q within the first differently-focused image coincides with the position of the point Q within the second differently-focused image. FIGS. 8A and 8B illustrates a change in pixel value along the line segment PQ within each differently-focused image. In FIGS. 8A and 8B, the horizontal axis indicates the pixel position, and the vertical axis indicates the pixel value at the corresponding pixel position.

In this case, the pixel value changes to a large extent at the position of the blood vessel (i.e., an intermediate position between the point P and the point Q) as compared with an area (e.g., mucous membrane (i.e., tissue)) other than the blood vessel. Therefore, the G and B pixel values of the first differently-focused image significantly decrease at an intermediate position between the point P and the point Q (see G1 and B1 in FIG. 8A). On the other hand, the G and B pixel values of the second differently-focused image that is not in focus gradually change (i.e., a change in pixel value (slope) with respect to a change in pixel position is small) at an intermediate position between the point P and the point Q (see G2 and B2 in FIG. 8B).

Figure 8C:
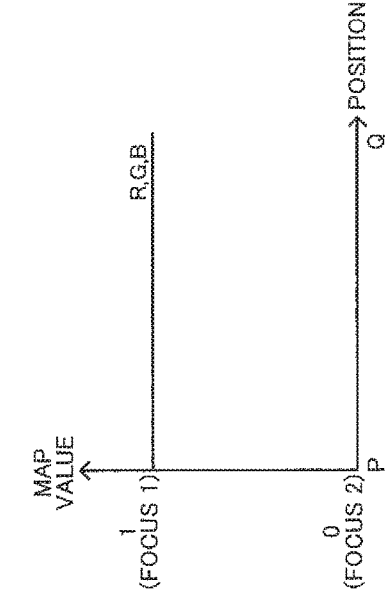

Therefore, when the evaluation value e (contrast value) is calculated with respect to the G pixel and the B pixel using the information around the blood vessel, the evaluation value e1 is larger than the evaluation value e2 (e1>e2). Accordingly, when the evaluation value E is calculated using E=e1-e2 or E=e1/e2, the evaluation value E satisfies E>E2 (see the expression (1)). FIG. 8C illustrates the above state (see G and B). FIG. 8C is a graph illustrating the values of the first synthesis map calculated from the R signal, the G signal, and the B signal with respect to the pixels situated along the line segment PQ. Since the evaluation value can be accurately calculated with respect to each differently-focused image with regard to the G signal and the B signal (see above), the first synthesis map based on the evaluation value has an appropriate value (i.e., a value (vertical axis=1) that represents that the first differently-focused image is used).

Specifically, a considerable problem does not occur with respect to the G signal and the B signal even when the first synthesis map MF is used for the synthesis process (i.e., even when the synthesis process with respect to the current frame is performed using only the information obtained from the current frame) in the same manner as in the known method. FIG. 8E is a view illustrating the pixel values of the synthesized image obtained by synthesizing the first differently-focused image illustrated in FIG. 8A and the second differently-focused image illustrated in FIG. 8B using the first synthesis map illustrated in FIG. 8C. As illustrated in FIG. 8E, the G signal and the B signal have values similar to those of the first differently-focused image illustrated in FIG. 8A (an appropriate image has been selected).

On the other hand, the color of a blood vessel includes the R signal to only a small extent (see above). When the user observes the color image illustrated in FIG. 7A, it is obvious that there is an object that is situated in the center area of the image and extends in the vertical direction. However, this state is not sufficiently reflected in the R pixel value. Specifically, even when the image is in focus, the R signal changes in pixel value to only a small extent in the blood vessel area as compared with the G signal and the B signal (see R1 in FIG. 8A). When the image is out of focus, a change in pixel value may become small, and it may be difficult to distinguish a change in pixel value from noise (see R2 in FIG. 8B).

In this case, a change in R value in FIG. 8A is very small, and it is difficult to accurately distinguish a change in R value from noise. Therefore, when the evaluation value e is calculated using the R pixel value illustrated in FIG. 8A and the R pixel value illustrated in FIG. 8B, a significant difference is observed between the evaluation value e1 and the evaluation value e2. As a result, the evaluation value satisfies E1<E<E2 (see the expression (1)), and the value MF is calculated to be 0.5 (see R in FIG. 8C), for example.

Therefore, when the synthesis process is performed with respect to the current frame using the first synthesis map in the same manner as in the known method, the R pixel value of the synthesized image is calculated to be the average value of the R pixel value (R1) of the first differently-focused image and the R pixel value (R2) of the second differently-focused image (FIG. 8E). As is clear from comparison between R1 in FIG. 8A and (R1+R2)/2 in FIG. 8E, a change in pixel value in the blood vessel area further decreases due to the synthesis process. Since the color of a color image is determined by the ratio of the R, G, and B pixel values, the user observes a significant change in color even when a change in pixel value is small. According to the known method that uses only the information obtained from the current frame, it is impossible to perform an appropriate synthesis process with respect to a frame in which an image is captured using specific illumination light, and the color of the object (e.g., blood vessel) becomes unnatural.

Although an example in which the two differently-focused images are synthesized when there is no difference between the evaluation value e1 and the evaluation value e2 has been described above, either the first differently-focused image or the second differently-focused image may be necessarily selected (i.e., the value of the first synthesis map may be limited to "0" or "1") depending on the synthesis method. In such a case, the second differently-focused image may be selected (i.e., the value of the first synthesis map may be set to "0") since there is no difference between the evaluation value e1 and the evaluation value e2. As a result, the R pixel value calculated by the synthesis process may coincide with the R pixel value illustrated in FIG. 8B (i.e., the R pixel value calculated by the synthesis process may be smaller than the R pixel value illustrated in FIG. 8E), and the object may be displayed in a more inappropriate color.

On the other hand, the method according to the first embodiment uses the second synthesis map when performing the synthesis process instead of the first synthesis map. The second synthesis map is calculated by performing the weighted averaging process on a plurality of first synthesis maps using a given weight. For example, the second synthesis map represents the average value of the value of the first synthesis map with respect to the G signal and the value of the first synthesis map with respect to the B signal (see FIG. 6 (table) and the expression (3)). Therefore, the R, G, and B values of the second synthesis map are set to "1" along the line segment PQ (see FIG. 8D).

Figure 8D:
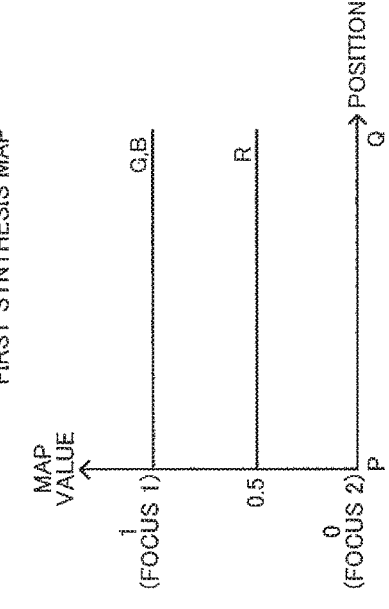
Figure 8F:
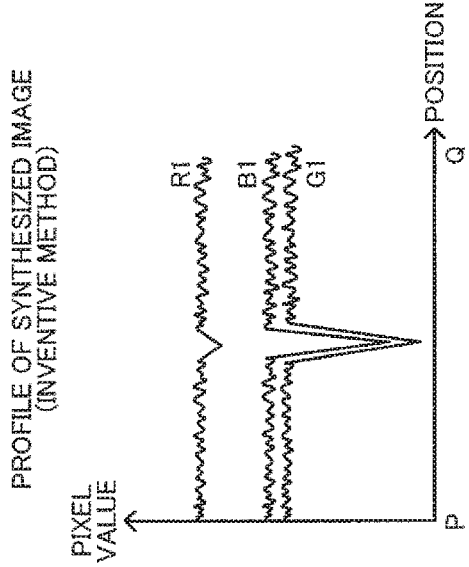
Figure 8E:
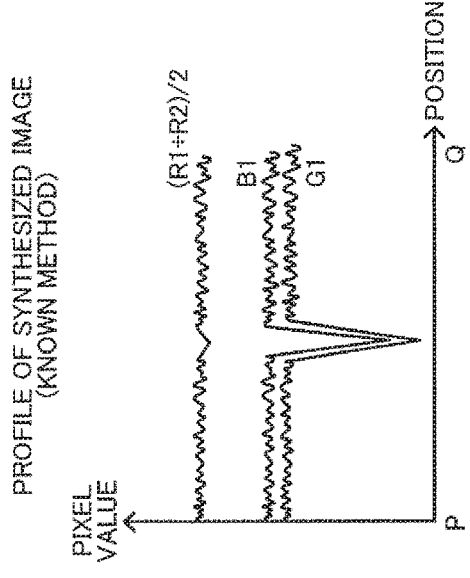

FIG. 8F is a view illustrating the pixel values of the synthesized image obtained by synthesizing the first differently-focused image illustrated in FIG. 8A and the second differently-focused image illustrated in FIG. 8B using the second synthesis map illustrated in FIG. 8D. Since the values of the second synthesis map are set to "1" along the line segment PQ, the pixel values obtained by the synthesis process are the same as the pixel values of the first differently-focused image (i.e., FIG. F coincides with FIG. 8A).

Specifically, the method according to the first embodiment can appropriately select the differently-focused image that is in focus (see FIG. 7A).

It may be considered in view of the above description that the R signal (i.e., a signal that corresponds to a color that does not easily forms contrast in a broad sense) may be unnecessary. Specifically, when contrast is not obtained with respect to a specific channel (e.g., R), a plurality of R differently-focused images should be out of focus, and it may be considered that the R image cannot be brought into focus by the synthesis process (i.e., the R image does not affect the resulting color image irrespective of the synthesis process).

However, it is unlikely that a given color does not contribute to a given object. It is unlikely that a situation in which the R signal is "0" occurs although the G signal and the B signal are mainly used, and it is considered that the R signal necessarily forms the object. The R signal may not be distinguished from noise within a differently-focused image that is out of focus (see FIG. 8B), but has some value within a differently-focused image that is in focus (see FIG. 8A).

Specifically, since even a color that does not easily forms contrast, may form contrast, it is necessary to select an appropriate differently-focused image. The color is determined by the ratio of the signal that corresponds to each channel (see above). Therefore, the effect of the R signal on the color should not be disregarded although the degree of contribution of R to the formation of contrast is low as compared with G and B. For example, a change in R pixel value is small in FIGS. 8E and 8F. However, while a natural color (i.e., a color that is normally observed as the color of a blood vessel when an in vivo image is captured) is obtained in FIG. 8F, an unnatural color is obtained in FIG. 8E.

The above description may bring up another question. Specifically, it may be considered that, when a color that does not easily forms contrast differs between a differently-focused image that is in focus and a differently-focused image that is out of focus, the difference can be detected using only the R signal in the same manner as in the known method (i.e., an appropriate synthesis process can be performed using only the first synthesis map).

However, a change in R signal is very small (see R1 in FIG. 8A). Moreover, the degree of noise mixed changes corresponding to the situation. Therefore, when the contrast value is calculated from each differently-focused image, it is difficult to determine whether the contrast has occurred due to noise or a change in signal value, and evaluate a plurality of differently-focused images using the contrast value. Specifically, it is difficult to accurately perform the synthesis process with respect to a color that does not easily forms contrast (see above). Since a change in G and B signal values is very large as compared with a change in signal value due to noise, it is possible to accurately perform the synthesis process, and it is advantageous to also use the information about the G or B signal instead of performing the synthesis process using only the R signal.

As described above, when images captured in a frame in which illumination light having a color that does not easily forms the contrast of the object is used, are synthesized based on the value of the synthesis map calculated with respect to a frame in which another illumination light is used, it is possible to implement a highly accurate image synthesis process independently of the color of the object and the color of the illumination light.

Figure 9:
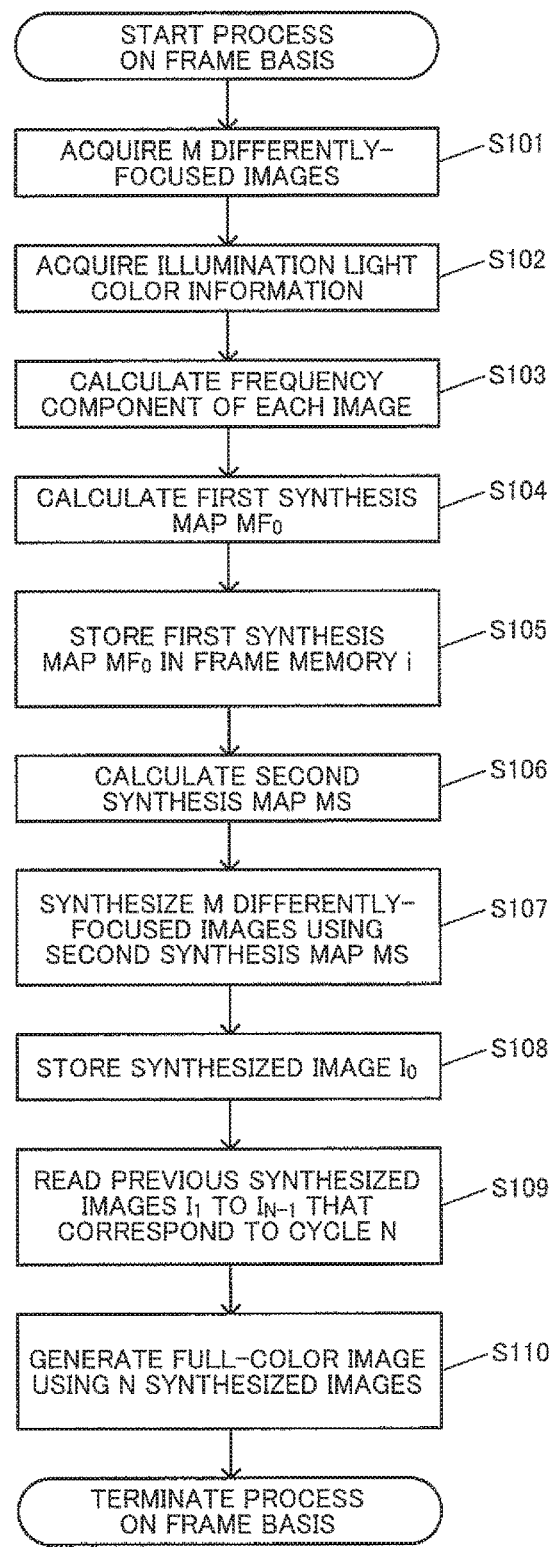
FIG. 9 is a flowchart illustrating a process (first embodiment).
Figure 10:
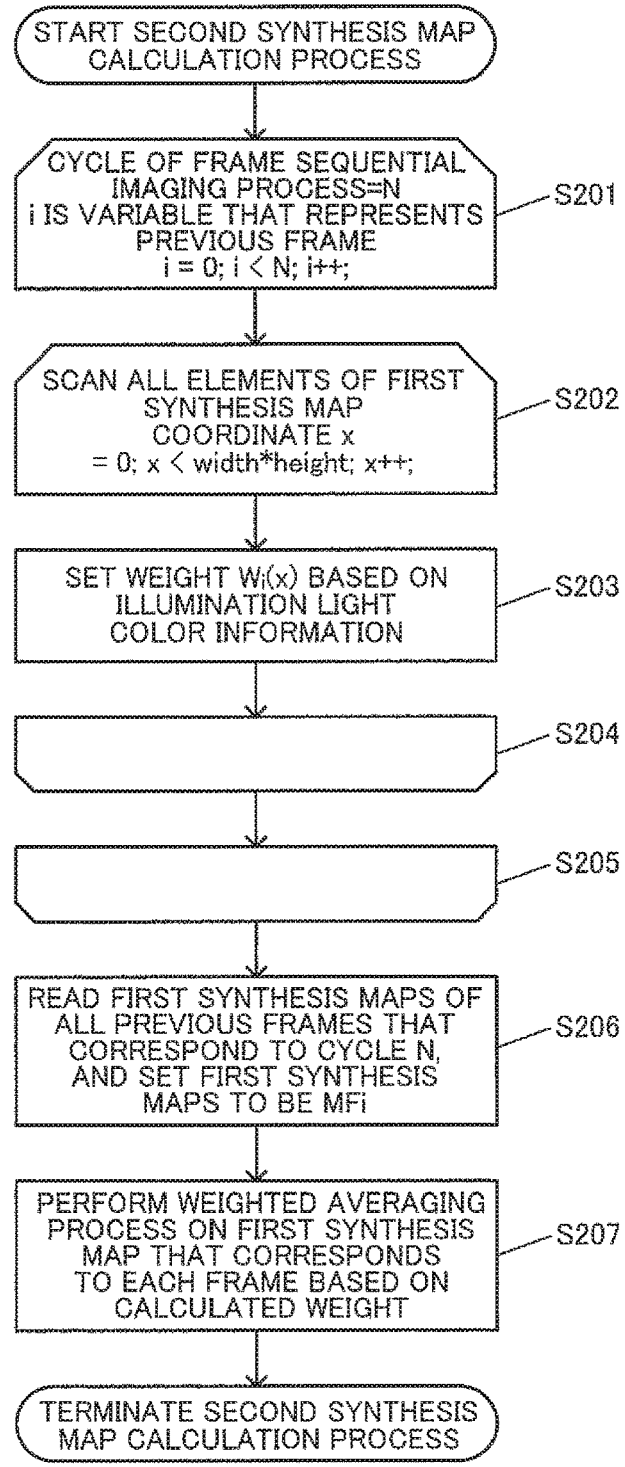
FIG. 10 is a flowchart illustrating a second synthesis map calculation process (first embodiment).

FIGS. 9 and 10 are flowcharts illustrating the process according to the first embodiment. FIG. 9 illustrates the process that is performed every frame. In the process illustrated in FIG. 9, M differently-focused images are acquired (S101). The illumination light color information that represents the illumination light applied when the M differently-focused images acquired in the step S101 were captured, is acquired (S102). The illumination light color information may be the label described above. When R, G, and B are used, the illumination light color information is information that represents a value "0", "1", or "2".

A frequency component (contrast value or evaluation value) is calculated with respect to each of the plurality of differently-focused images (S103), and the first synthesis map MF0 with respect to the current frame is calculated based on the frequency component (S104). The frequency component is calculated using a band-pass filter or the like (see above), and the first synthesis map MF0 is calculated using the expression (1) or the like. The first synthesis map MF0 calculated as described above is stored in the frame memory (first synthesis map frame memory 323).

When the first synthesis map MF0 has been calculated, the second synthesis map MS that is used for the synthesis process is calculated (S106). FIG. 10 is a flowchart illustrating the second synthesis map calculation process. When the second synthesis map calculation process has started, a loop corresponding to the number N of frames that is included in one cycle of the frame sequential imaging process is performed (S201). Specifically, the process between the step S201 and the step S205 is repeated corresponding to one cycle.

In the step S201, all of the pixels of the first synthesis map (i.e., all of the pixels of the captured image) are scanned, and the weight Wi that is used when calculating the second synthesis map is set to each pixel. In the example illustrated in FIG. 10, the pixels are updated by one pixel in the steps S202 and S204 from the start point to the end point. The process that sets the weight Wi(x) to the processing target pixel based on the illumination light color information (S203) is performed during the loop.

The weights W0, W1, W2, . . . , and WN−1 are calculated by the steps S201 to S205. The previous first synthesis maps that correspond to one cycle are read from the frame memory (first synthesis map frame memory 323), and set to be MF1, MF2, . . . , and MFN−1 (S206).

The weighted averaging process is performed on the first synthesis map MF0 with respect to the current frame that has been calculated by the step S104, and the first synthesis maps MF1, MF2, . . . , and MFN−1 that have been read in the step S206, using the weights W0, W1, W2, . . . , and WN−1 that have been calculated by the steps S201 to S205. The weighted averaging process is performed using the expression (3), for example.

When the second synthesis map MS has been calculated, M differently-focused images are synthesized using the second synthesis map MS to calculate a synthesized image I0 (S107), and the calculated synthesized image I0 is stored in the frame memory (image synthesis frame memory 326) (S108).

The previous synthesized images I1, I2, . . . , and IN−1 that correspond to one cycle are read (S109), and a full-color image is generated using the synthesized image I0 and the previous synthesized images I1, I2, . . . , and IN−1 (S110).

According to the first embodiment, the processing section 320 included in the image processing device 300 calculates the second synthesis map based on the first synthesis map that has been calculated with respect to the i-th frame, and the first synthesis map that has been calculated with respect to the k-th frame that temporally precedes the i-th frame. The processing section 320 performs the synthesis process that synthesizes the plurality of images that were captured in the i-th frame and differ from each other as to the in-focus object plane position, based on the second synthesis map.

According to this configuration, it is possible to utilize the first synthesis map calculated with respect to a frame that precedes the current frame (processing target frame) when calculating the second synthesis map with respect to the current frame (see above). This makes it possible to accurately calculate the second synthesis map even when the reliability of the first synthesis map MF0 calculated with respect to the current frame is low. In particular, when the second synthesis map calculation process and the synthesis process that utilizes the second synthesis map are sequentially performed with respect to the latest frame (e.g., real-time process), the first synthesis map calculation process is performed with respect to each frame. Specifically, since the first synthesis map has been calculated with respect to the previous frame, it suffices to store and read the first synthesis map with respect to the previous frame instead of performing the first synthesis map calculation process with respect to the previous frame in the current frame, and it is possible to implement an efficient process.

Although an example in which the information obtained from the previous frame is used during the process performed on the current frame has been described above, various modifications and variations may be made of the process according to the first embodiment. Specifically, when a given frame is the processing target frame, the first synthesis map calculated with respect to a frame that temporally follows the given frame may be used for the process.

For example, when it is desired to find a lesion using an endoscope apparatus and then remove the lesion, it is necessary to display the captured image while reducing a delay as much as possible. In such a case, it is necessary to perform the synthesis process on the latest frame (current frame), and immediately display the synthesized image, and a previous frame is inevitably used to implement the process. However, when it is desired to perform only a lesion screening process, the captured images may be stored, and viewed by the user (doctor) after some time has elapsed. For example, images captured by a capsule endoscope are stored in a receiver or the like possessed by the user, and may be viewed after completion of observation (i.e., after the capsule endoscope has discharged from the body).

In this case, since a plurality of differently-focused images have been acquired over a plurality of frames before the process is started, it is unnecessary to start the first synthesis map calculation process and the second synthesis map calculation process from a frame that temporally precedes the current frame. For example, the process may be started from the last frame, or a frame in which an object for which the degree of importance is high, is captured. In this case, the method according to the first embodiment is characterized in that the synthesis process is performed using information obtained from another frame (another wavelength band) instead of using only one frame (specific wavelength band). Specifically, a frame other than the processing target frame that temporally precedes or follows the processing target frame may be used for the process.

When the object and the imaging section undergo a relative motion between frames, it is not appropriate to use the first synthesis map over the frames (as described later in connection with the second embodiment). Therefore, when a frame other than the processing target frame is used, it is preferable not to use a frame that considerably temporally differs from the processing target frame in order to reduce the possibility that a motion occurs. Since it is desirable that no motion occurs (or the amount of motion be small), motion information between frames may be calculated, and a frame for which it has been determined that the relative motion of the object and the imaging section is small with respect to the processing target frame may be preferentially used for the process. The motion information may be a motion vector calculated from a plurality of images that differ from each other as to the acquisition timing, for example.

The processing section 320 may calculate the second synthesis map with respect to the i-th frame by synthesizing the first synthesis map with respect to the i-th frame and the first synthesis map with respect to the k-th frame while weighting the first synthesis maps using given weight information.

According to this configuration, when the first synthesis maps have been calculated with respect to the processing target frame and another frame, it is possible to calculate the second synthesis map by performing a weighted synthesis process on the first synthesis maps. Specifically, the weighted addition process may be performed on the first synthesis maps (see the expression (3)).

The imaging section 200 may perform the frame sequential imaging process in which one cycle includes an R frame, a G frame, and a B frame, and the processing section 320 may set the weight information that increases a weight that is applied to the first synthesis map that corresponds to the G frame or the B frame as compared with the first synthesis map that corresponds to the R frame.

This makes it possible to perform an accurate synthesis process even when the R signal does not easily form contrast when R, G, and B are used. The weight information illustrated in FIG. 6 may be used as the weight information. In the example illustrated in FIG. 6, the weight that corresponds to R is set to "0", the weight that corresponds to G is set to "0.5", and the weight that corresponds to B is set to "0.5". This process is useful when the observation target is a blood vessel within an in vivo image (see above).

The processing section 320 may calculate the second synthesis map with respect to the i-th frame based on the first synthesis map calculated with respect to the i-th frame, and the first synthesis maps calculated with respect to the first to (i−1)-th frames and the (i+1)-th to N-th frames.

This makes it possible to calculate the second synthesis map with respect to a given frame using signals that correspond to one cycle of the frame sequential imaging process. For example, when R, G, and B are used, the G frame and the B frame are referred to when calculating the second synthesis map that corresponds to the R frame, the B frame and the R frame are referred to when calculating the second synthesis map that corresponds to the G frame, and the R frame and the G frame are referred to when calculating the second synthesis map that corresponds to the B frame. Note that the frame that is referred to (i.e., a frame that differs from the processing target frame) may be a frame that temporally precedes or follows the processing target frame. Therefore, when light is applied in order from R1→G1→B1→R2→G2→B2, . . . , and the second synthesis map that corresponds to the R2 frame is calculated, (G1, B1), (B1,G2), or (G2,B2) may be referred to. According to this configuration, since information about all of the colors (all of the wavelength bands) that can be captured is used, it is possible to accurately calculate the second synthesis map.

The processing section 320 may generate an i-th synthesized image by performing the synthesis process that synthesizes the plurality of images that were captured in the i-th frame and differ from each other as to the in-focus object plane position, based on the second synthesis map, and synthesize the first to N-th synthesized images that correspond to the first to N-th frames to generate an output image (display image or full-color image).

According to this configuration, when the synthesized image (all-in-focus image) has been calculated with respect to each frame, it is possible to generate a full-color image by synthesizing the images that correspond to one cycle in the same manner as in the case of using a common frame sequential imaging method. Specifically, the process illustrated in FIG. 4 may be performed.

The first embodiment may be applied to the image processing device 300 that includes the image acquisition section 310 that acquires captured images from the imaging section 200 that performs a frame sequential imaging process in which one cycle includes first to N-th (wherein N is an integer equal to or larger than 3) frames that include at least an R frame, a G frame, and a B frame, and the processing section 320 that performs a synthesis process that synthesizes the captured images based on a synthesis map. The image acquisition section 310 acquires the captured images that have been captured by the imaging section 200 in an i-th (wherein i is an integer that satisfies 1≤i≤N) frame and differ from each other as to the in-focus object plane position, the processing section 320 calculates the synthesis map with respect to the i-th frame that corresponds to R based on the synthesis map calculated with respect to the frame that corresponds to G and the synthesis map calculated with respect to the frame that corresponds to B when the i-th frame is a frame that corresponds to R, and the processing section 320 performs the synthesis process that synthesizes a plurality of images that have been captured in the i-th frame and differ from each other as to the in-focus object plane position, based on the synthesis map.

Note that R, G, and B respectively refer to red (R), green (G), and blue (B) (i.e., the three primary colors of light) (see above), and the R frame, the B frame, and the G frame refer to frames in which the captured image was acquired by application of light having the corresponding color (wavelength band). The wavelength band of each light (R, G, and B) may be modified in various ways. For example, the wavelength band of each light (R, G, and B) may be the band illustrated in FIGS. 3A to 3C.

According to this configuration, it is possible to implement an image processing device that calculates the second synthesis map based on the information about at least one of G and B when the frame sequential imaging process that captures (only) R, G, and B is performed, and the processing target frame corresponds to R. In the example illustrated in FIG. 6 (table), the first synthesis map calculated from the R signal is not referred to irrespective of the value of the label. Specifically, when the current frame corresponds to R, the first synthesis map calculation process and the first synthesis map storage process performed with respect to the current frame may be skipped. In this case, since part of the process can be skipped, it is possible to reduce the processing load, or suppress a decrease in memory capacity, for example.

The first embodiment may also be applied to an endoscope apparatus that includes the imaging section 200 and the image processing device 300 described above (see FIG. 1).

In this case, it is likely that an in vivo image is captured and observed, and it is possible to appropriately deal with the above problem with regard to a blood vessel.

The image processing device and the like according to the first embodiment may include a processor and a memory. The processor may implement the function of each section by means of individual hardware, or may implement the function of each section by means of integrated hardware, for example. For example, the processor may include hardware, and the hardware may include at least one of a circuit that processes a digital signal and a circuit that processes an analog signal. For example, the processor may include one or more circuit devices (e.g., IC), and one or more circuit elements (e.g., resistor or capacitor) that are mounted on a circuit board. The processor may be a central processing unit (CPU), for example. Note that the processor is not limited to a CPU. Various other processors such as a graphics processing unit (GPU) or a digital signal processor (DSP) may also be used. The processor may be a hardware circuit that includes an ASIC. The processor may include an amplifier circuit, a filter circuit, and the like that process an analog signal. The memory may be a semiconductor memory (e.g., SRAM or DRAM), a register, a magnetic storage device (e.g., hard disk drive), or an optical storage device (e.g., optical disk device). For example, the memory stores a computer-readable instruction, and each section of the image processing device and the like is implemented by causing the processor to execute the instruction. The instruction may be an instruction included in an instruction set that is included in a program, or may be an instruction that causes a hardware circuit included in the processor to operate.

3. Second Embodiment

Figure 11:
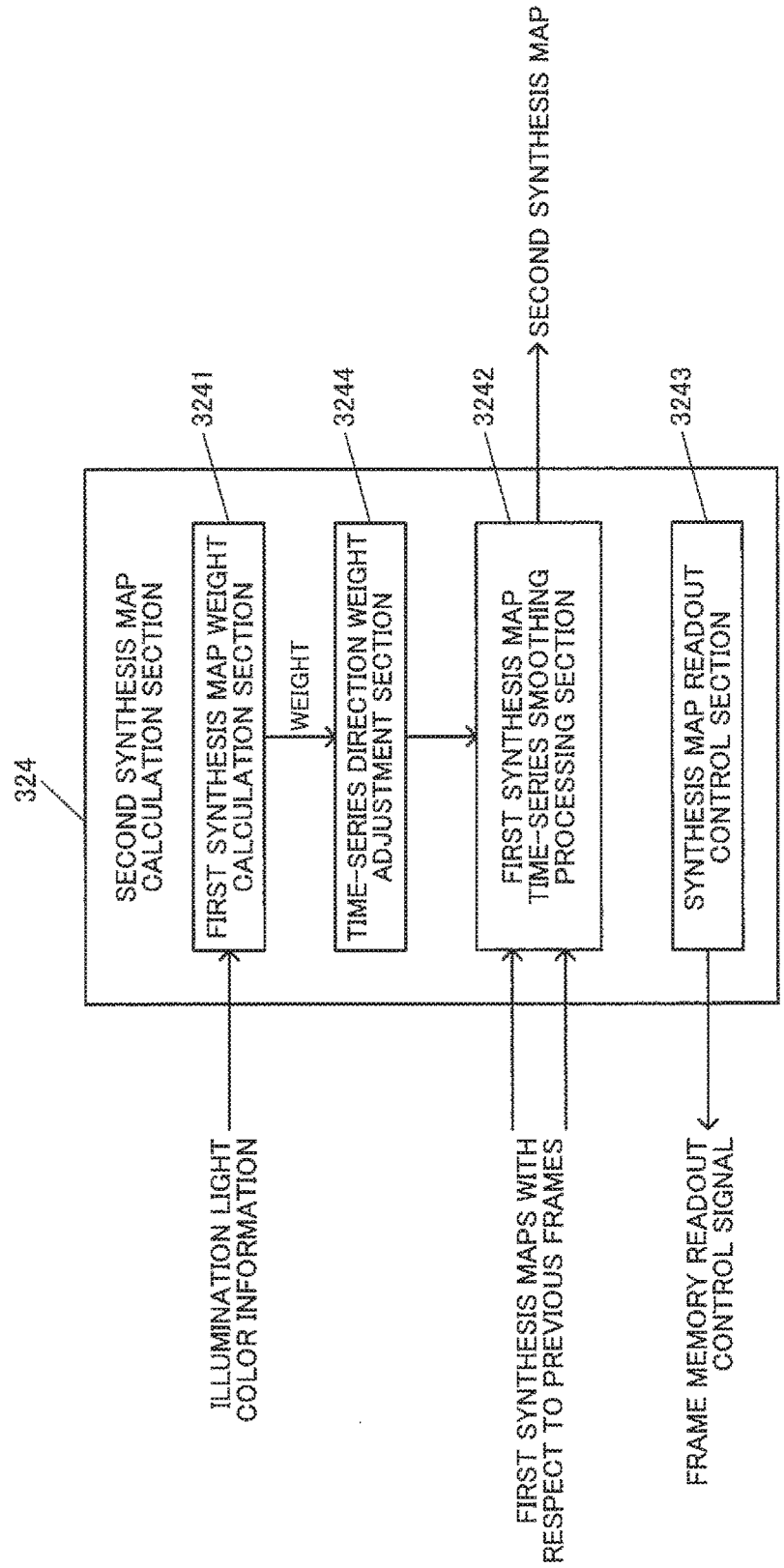
FIG. 11 is a flowchart illustrating a second synthesis map calculation section (second embodiment).

FIG. 11 illustrates a configuration example of the second synthesis map calculation section 324 according to the second embodiment. The second synthesis map calculation section 324 is configured in the same manner as in the first embodiment, except for the feature illustrated in FIG. 11. In the second embodiment, the second synthesis map calculation section 324 includes a time-series direction weight adjustment section 3244 in addition to the elements described above in connection with the first embodiment (see FIGS. 1 and 11).

The time-series direction weight adjustment section 3244 multiplies the weight Wi calculated by the first synthesis map weight calculation section 3241 by a time-series direction adjustment coefficient Ci to overwrite the weight Wi. The weight Wi (before being overwritten) and the time-series direction adjustment coefficient Ci are set to satisfy the following expression (5).

$$\sum_{i=0}^{N-1} C_i(x) \times W_i(x) = 1 \tag{5}$$

It is preferable that the sum of the weight applied to each first synthesis map be "1" (see the expression (2) described above in connection with the first embodiment). In the second embodiment, since the weight is overwritten with the value Wi×Ci (i.e., the value Wi×Ci is used as the weight), the condition that corresponds to the expression (2) can be satisfied by the expression (5).

When R, G, and B are used (N=3), the adjustment coefficients C0(x), C1(x), and C2(x) are used. In the second embodiment, it is desirable that the adjustment coefficient C increase as the value i decreases. FIG. 12 (table) illustrates an example of the adjustment coefficient C and the final weight Ci×Wi. In the example illustrated in FIG. 12, the adjustment coefficient is set so that the degree of priority of a signal that is other than the R signal and is closer to the current frame is increased. Note that the value Wi illustrated in FIG. 6 is used as the value Wi.

Specifically, when the label is set to "0", the value C0 is decreased since the current frame is "R", and the value C1 that is closer to the current frame is increased since the values C1 and C2 do not correspond to R. In the example illustrated in FIG. 12, C0=0, C1=2, and C2=0 when the label is set to "0". When the label is set to "1" or "2", the value C0 is set to "2" since the current frame is "G" or "B", and the values C1 and C2 are set to "0".

The final weight Ci×Wi is set as illustrated in FIG. 12 when the adjustment coefficient C and the value W illustrated in FIG. 6 are used. When the label is set to "0", the weight applied to the first synthesis map with respect to the B signal in the preceding frame is set to "1", and the remaining weights are set to "0". When the label is set to "1", the weight applied to the first synthesis map with respect to the G signal in the current frame is set to "1", and the remaining weights are set to "0". When the label is set to "2", the weight applied to the first synthesis map with respect to the B signal in the current frame is set to "1", and the remaining weights are set to "0".

According to this configuration, it is possible to increase the degree of priority (increase the weight) with respect to the first synthesis map that is close to the current frame in time series on the assumption that the weight set to the R signal is relatively decreased. The method according to the invention described above uses the synthesis map calculated with respect to another frame when performing the synthesis process with respect to a given frame. However, the synthesis map with respect to a previous frame reflects the in-focus state in the previous frame. Therefore, when the in-focus state differs between the previous frame and the current frame, it is inappropriate to use the synthesis map with respect to the previous frame for the current frame.

For example, when the object has changed (e.g., the object or the imaging section has moved) between the previous frame and the current frame, or when the relative positional relationship between the object and the imaging section has changed between the previous frame and the current frame although the object is identical, it is inappropriate to use the synthesis map with respect to the previous frame for the current frame.

There is a tendency that a relative motion of the object easily occur when the time between the frames is long. Specifically, when the frame for which the first synthesis map has been calculated is temporally distant from the current frame, it is likely that high accuracy cannot be obtained when the first synthesis map with respect to the previous frame is used for the current frame. On the other hand, when the frame for which the first synthesis map has been calculated is temporally close to the current frame, it is likely that the first synthesis map with respect to the previous frame can be used with high accuracy. Specifically, it is desirable to use time-series information with respect to the current frame in order to adjust the weight.

The adjustment coefficient C according to the second embodiment is set taking the above point in to consideration. Since the adjustment coefficient C is increased as the value i decreases, it is possible to increase the degree of contribution of the first synthesis map calculated with respect to a frame that is temporally close to the current frame.

Figure 13:
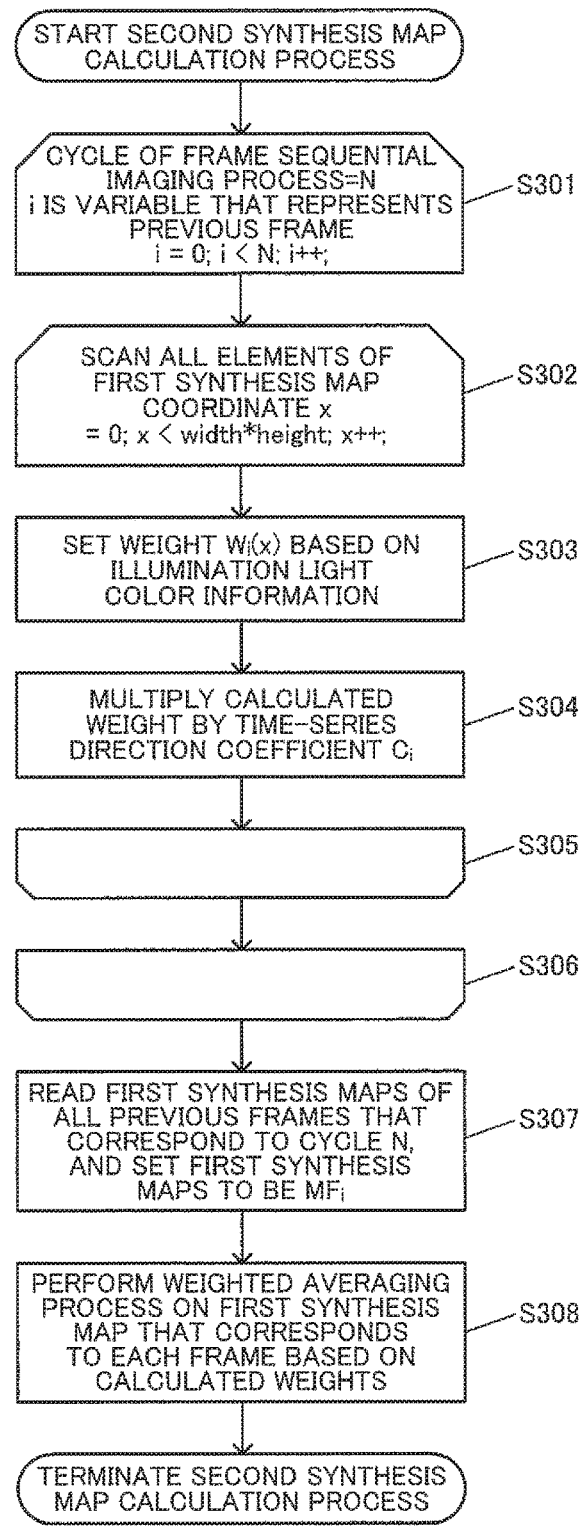
FIG. 13 is a flowchart illustrating a second synthesis map calculation process (second embodiment).

FIG. 13 is a flowchart illustrating the second synthesis map calculation process according to the second embodiment. The steps S301 to S303 illustrated in FIG. 13 are the same as the steps S201 to S203 illustrated in FIG. 10. In the second embodiment, after the weight Wi has been set in the step S303, the weight Wi is multiplied by the time-series direction adjustment coefficient C (S304). Since the step S304 is included in the loop performed in the step S301 and the loop performed in the step S302, the step S304 is performed on a pixel basis with respect to the information that corresponds to one cycle.

The weight that has been adjusted in the time-series direction is calculated by the step S306. The subsequent steps S307 and S308 are the same as the steps S206 and S207 illustrated in FIG. 10.

According to the second embodiment, the processing section 320 calculates the second synthesis map using the weight information that increases the weight applied to the first synthesis map calculated with respect to a frame that is temporally close to the i-th frame.

According to this configuration, since the weight applied to a frame that is temporally close to the i-th frame is increased, it is possible to suppress the effect of a relative motion of the object and the imaging section, and the like, and perform an accurate synthesis process. Specifically, the adjustment coefficients C0 to C2 illustrated in FIG. 12 may be used. Note that the expression "temporally close to" used herein refers to the time difference with respect to the processing target frame, and a frame for which the first synthesis map is calculated may temporally precede or follow the processing target frame (as described above in connection with the first embodiment). Therefore, a frame that immediately follows the processing target frame and a frame that immediately precedes the processing target frame need not be distinguished from each other as long as a special situation does not exist.

The expression "temporally close to the i-th frame" means that the time difference (or the frame difference) between the timing of the target frame and the timing of the i-th frame is small. For example, when an (i+p)-th frame has been acquired after p frames have temporally elapsed from the i-th frame, an (i+q)-th frame has been acquired after q frames have temporally elapsed from the i-th frame, and p<q, the (i+p)-th frame is temporally closer to the i-th frame than the (i+q)-th frame. When an (i+p)-th frame has been acquired after a time tp has elapsed from the acquisition timing of the i-th frame, an (i+q)-th frame has been acquired after a time tq has elapsed from the acquisition timing of the i-th frame, and tp<tq, the (i+p)-th frame is temporally closer to the i-th frame than the (i+q)-th frame.

A change with respect to the processing target frame (i-th frame) may be a change that precedes or follows the processing target frame. Therefore, the expression "after p frames have elapsed" or "a time tp has elapsed" may be considered to be "before p frames" or "before a time tp" (i.e., "after −p frames have elapsed" or "a time −tp has elapsed" with regard to a temporal change width with respect to the i-th frame. Specifically, whether or not a frame is "temporally close to the i-th frame" may be determined using the absolute value of the number of frames or time without taking account of the sign. For example, since |p|<|−q| when "after p frames have elapsed" and "before p frames (after −p frames have elapsed)" are compared, the former case is temporally closer to the i-th frame than the latter case. Since the weight is also applied to the i-th frame (see above), a case where p=0 may also be taken into consideration.

4. Third Embodiment

Figure 14:
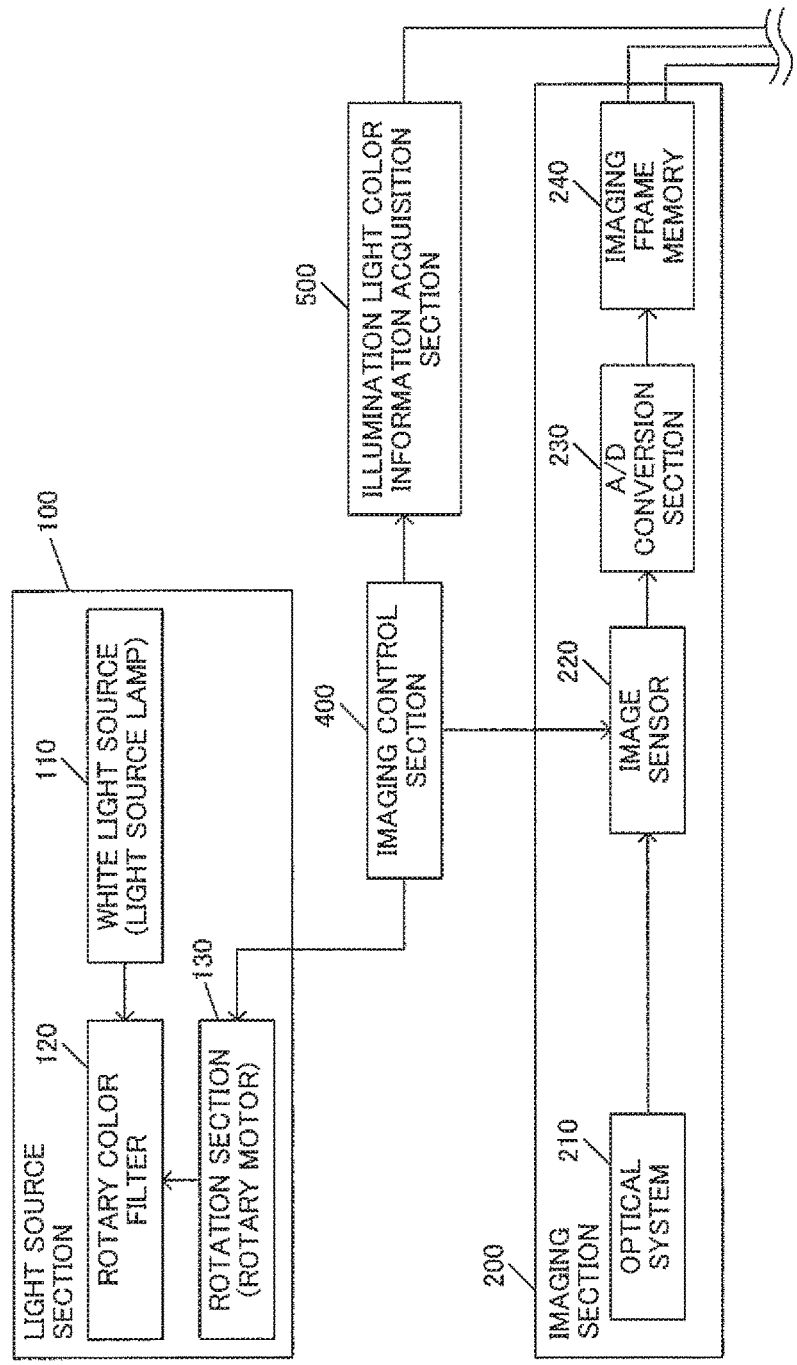
FIG. 14 illustrates a configuration example of an endoscope apparatus that includes an image processing device according to a third embodiment.

FIG. 14 illustrates a configuration example of an endoscope apparatus according to the third embodiment. As illustrated in FIG. 14, the endoscope apparatus according to the third embodiment includes a threshold value determination section 328 in addition to the elements illustrated in FIG. 1 that have been described above in connection with the first embodiment, and the first synthesis map frame memory 323 is replaced by a second synthesis map frame memory 329. The second synthesis map calculation section 324 according to the third embodiment includes a synthesis map weight calculation section 3245, a synthesis map time-series smoothing processing section 3246, and a synthesis map readout control section 3243.

Note that description of the same features as those described above in connection with the first embodiment are omitted, and the configuration that differs from the configuration described above in connection with the first embodiment is described in detail below. In the third embodiment, the first synthesis map frame memory 323 is replaced by the second synthesis map frame memory 329. Specifically, when the second synthesis map has been calculated with respect to a given frame, the second synthesis map is stored in the memory. Therefore, the synthesis map time-series smoothing processing section 3246 that outputs the second synthesis map is connected to the image synthesis processing section 325 and the second synthesis map frame memory 329.

In the third embodiment, the second synthesis map with respect to the current frame is calculated using the first synthesis map with respect to the current frame, and the second synthesis map with respect to a previous frame. In this case, it is unnecessary to use all of the second synthesis maps with respect to the previous frames (i.e., frames that precede the current frame by 1 to N–1 frames) that correspond to one cycle. For example, the second synthesis map with respect to the frame that immediately precedes the current frame may be used.

Specifically, the second synthesis map that has been calculated using the method according to the first embodiment or the second embodiment is information based on the first synthesis maps that correspond to one cycle. Since the second synthesis map is a synthesis map that has been determined to be appropriate (highly accurate) taking account of a plurality of frames, it is considered that the second synthesis map can also be used for the current frame with high accuracy unless an exceptional situation has occurred. The term "exceptional situation" used herein refers to a situation in which the object has made a motion between the current frame and the frame that immediately precedes the current frame, a situation in which an appropriate image was not acquired during the last cycle due to a breakdown of the device, or the like. It is unlikely that such an exceptional situation occurs.

Since the first synthesis map is calculated using only information obtained from one frame, the first synthesis map includes information having low reliability (e.g., a frame that corresponds to R). On the other hand, since the second synthesis map includes information obtained from a plurality of frames, and has high reliability, a considerable advantage is not obtained when a plurality of previous second synthesis maps are used when calculating the second synthesis map with respect to the current frame.

Therefore, the weight W0 applied to the first synthesis map MF0 calculated with respect to the current frame, and the weight W1 applied to the second synthesis map MS1 calculated with respect to the frame that immediately precedes the current frame, are used in connection with the third embodiment. The synthesis map time-series smoothing processing section 3246 included in the second synthesis map calculation section 324 calculates the second synthesis map MS0 with respect to the current frame using the following expression (6).

$$MS0(x) = W(x) \times MF0(x) + W1(x) \times MS1(x) \tag{6}$$

According to this configuration, since it suffices to store only the previous synthesis map that corresponds to one frame, the capacity of the frame memory can be reduced.

In the third embodiment, the reliability of the information obtained from the current frame may be determined using a threshold value. The weights (W0 and W1) that are used to calculate the second synthesis map may be changed based on the determination result.

The image processing device 300 according to the third embodiment includes the threshold value determination section 328 (see above). The threshold value determination section 328 determines whether or not the evaluation value e1(x) or e2(x) (contrast value in a narrow sense) of the frequency component calculated from each differently-focused image has exceeded a given threshold value thr, and generates a threshold value determination map TH(x). Specifically, the threshold value determination section 328 calculates the threshold value determination map TH(x) using the following expression (7). Note that max($\alpha$, $\beta$) in the expression (7) represents the larger of $\alpha$ and $\beta$.

$$TH(x) = \begin{cases} 0 & \max(e_1(x), e_2(x)) \le thr \\ 1 & \max(e_1(x), e_2(x)) > thr \end{cases} \tag{7}$$

The threshold value determination map TH(x) thus generated is output to the synthesis map weight calculation section 3245 included in the second synthesis map calculation section 324, and is used to determine the weight that is used when calculating the second synthesis map.

The synthesis map weight calculation section 3245 calculates the weight Wi(x) that is used to perform the weighted averaging process on the first synthesis map MF0 with respect to the current frame and the second synthesis map MS 1 with respect to the frame that immediately precedes the current frame based on the label of the illumination light color information and the threshold value determination map TH(x) using the table illustrated in FIG. 15A or 15B.

Specifically, the table illustrated in FIG. 15A is used for a pixel x for which TH(x)=0, and the table illustrated in FIG. 15B is used for a pixel x for which TH(x)=1. When TH(x)=1, at least one of the evaluation value e1(x) and the evaluation value e2(x) with respect to the pixel x is large to a certain extent (i.e., larger than the threshold value thr). Specifically, at least one of a plurality of differently-focused images captured in the current frame is in focus. Therefore, when the first synthesis map MF0 is calculated based on a plurality of differently-focused images acquired in the current frame, the first synthesis map MF0 can implement a highly accurate synthesis process. Specifically, when the first differently-focused image is in focus (e1(x)>thr), and the second differently-focused image is out of focus, E(x) ≥E2 (see the expression (1)), and MF(x)=1 (i.e., the first differently-focused image is synthesized in a ratio of 100%).

In this case, it is unnecessary to use information obtained from a previous frame since the reliability of the first synthesis map MF0 calculated with respect to the current frame is high, and a plurality of differently-focused images captured in the current frame may be synthesized using only the first synthesis map MF0. Therefore, the weight W0 is set to "1" and the weight W1 is set to "0" irrespective of the label (see FIG. 15B). Note that it suffices to increase the weight applied to the current frame, and the weight W0 need not necessarily be set to "1". For example, an optimum weight may be set experimentally corresponding to the color of the object.

When a blood vessel or the like within an in vivo image is observed, R does not easily form contrast (see above). However, an object other than a blood vessel may be captured, or the R signal may form contrast even when the object is a blood vessel when the imaging conditions (e.g., illumination light) have been changed. In the first embodiment and the second embodiment, the process is performed on the assumption that the degree of contribution of the R signal should be decreased since the R signal does not easily form contrast without taking a specific situation into consideration. On the other hand it is possible to determine whether or not contrast can be detected by the acquired signal by providing the threshold value determination section 328. Therefore, when the R signal forms sufficient contrast, it is possible to use the R signal for the synthesis process, for example.

When TH(x)=0, sufficient contrast may not be formed in each of a plurality of differently-focused images acquired in the current frame, the first synthesis map MF0 calculated from a plurality of differently-focused images acquired in the current frame may have low accuracy. Therefore, the weight applied to the current frame is decreased, and the weight applied to the previous frame is increased. For example, the weight W0 may be set to "0", and the weight W1 may be set to "1" (see FIG. 15A). Note that the weights used when TH(x)=0 are not limited to the example illustrated in FIG. 15A.

For example, the weights illustrated in FIG. 15 may be used when TH(x)=0. The table illustrated in FIG. 15C is provided to decrease the degree of contribution of the R signal, and increase the degree of priority with respect to information that is temporally close to the current frame (see the first embodiment and the second embodiment).

When the label is set to "0" (i.e., when the current frame is "R"), and the frame that immediately precedes the current frame is "B", the weight W0 is set to "0", and the weight W1 is set to "1" in the same manner as in FIG. 15A. In this case, the process is performed on the assumption that the reliability of the current frame is low, and the degree of contribution of the R signal should be decreased as much as possible.

When the label is set to "1" (i.e., when the current frame is "G"), and the frame that immediately precedes the current frame is "R", the weight W0 is set to "1", and the weight W1 is set to "0". In this case, since sufficient contrast is not formed in the current frame, the reliability of the first synthesis map MF0 calculated from the G signal may not be sufficiently high. However, the frame that immediately precedes the current frame is "R" (R signal). Therefore, when the second synthesis map MS1 with respect to the frame that immediately precedes the current frame is calculated using the method according to the first embodiment or the second embodiment, the process is performed using the first synthesis map MF2 calculated from the B signal acquired in the frame that immediately precedes the frame that immediately precedes the current frame, and the first synthesis map MF3 calculated from the G signal acquired in the frame that immediately precedes the frame for which the first synthesis map MF2 is calculated. When the second synthesis map MS1 is calculated using the table illustrated in FIG. 15C, the second synthesis map MS1 is calculated using the second synthesis map MS2 that corresponds to the B signal acquired in the frame that further precedes the current frame. In this case, the second synthesis map MS1 is apparently calculated with respect to the frame that immediately precedes the current frame, but is calculated using the information obtained from the frame that further precedes the current frame. Specifically, the difference from the current frame along the time axis is large, and a relative motion of the object may occur, for example. Therefore, a weight that increases the degree of priority with respect to the current frame is set in the example illustrated in FIG. 15C even when the evaluation value with respect to the current frame is equal to or smaller than the threshold value thr.

When the label is set to "2" (i.e., when the current frame is "B"), and the frame that immediately precedes the current frame is "G", the weight W0 is set to "0.5", and the weight W1 is set to "0.5". In this case, since the R signal is not used, it is unnecessary to decrease the degree of contribution of R. Since TH(x)=0, it is preferable to decrease the degree of contribution of the current frame, and increase the degree of contribution of the current frame as compared with the previous frame taking account of the time-series process. Therefore, an identical weight is set with respect to the current frame and the previous frame taking the balance therebetween into consideration.

The weights can thus be set using the threshold value determination map TH(x) that is the result of the threshold value determination process. The synthesis map readout control section 3243 according to the third embodiment reads the second synthesis map MS1 that has been stored with respect to the frame that immediately precedes the current frame. The synthesis map time-series smoothing processing section 3246 calculates the second synthesis map MS0 using the expression (6), and outputs the second synthesis map MS0.

Figure 16:
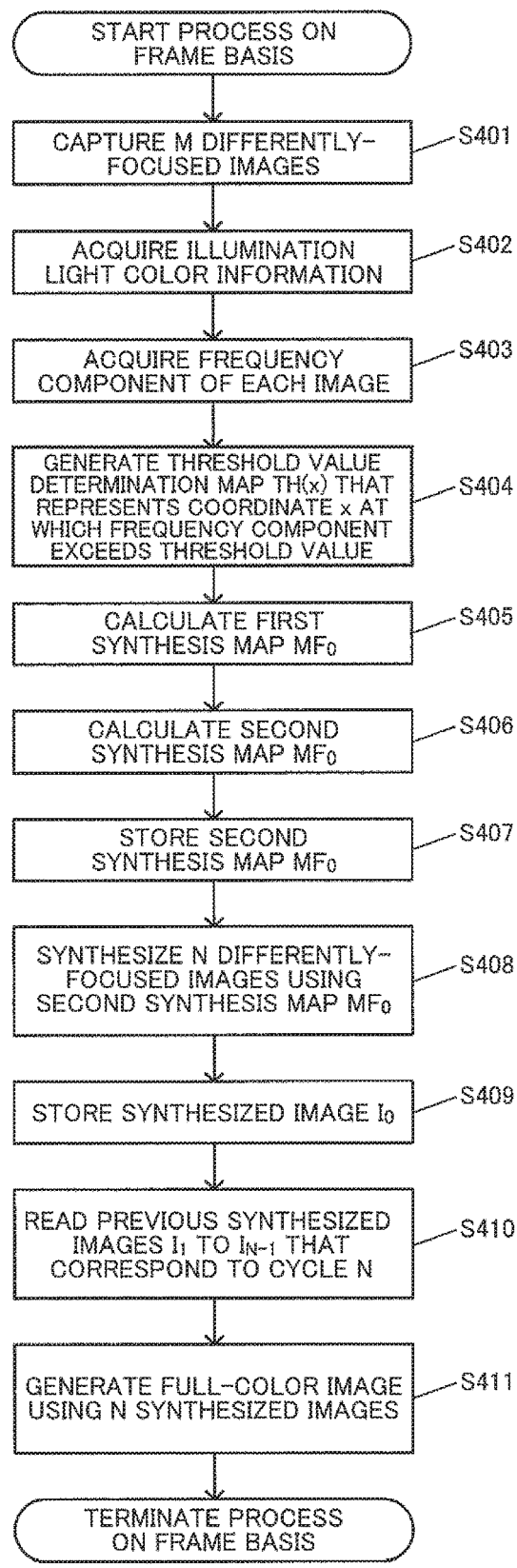
FIG. 16 is a flowchart illustrating a process (third embodiment).
Figure 17:
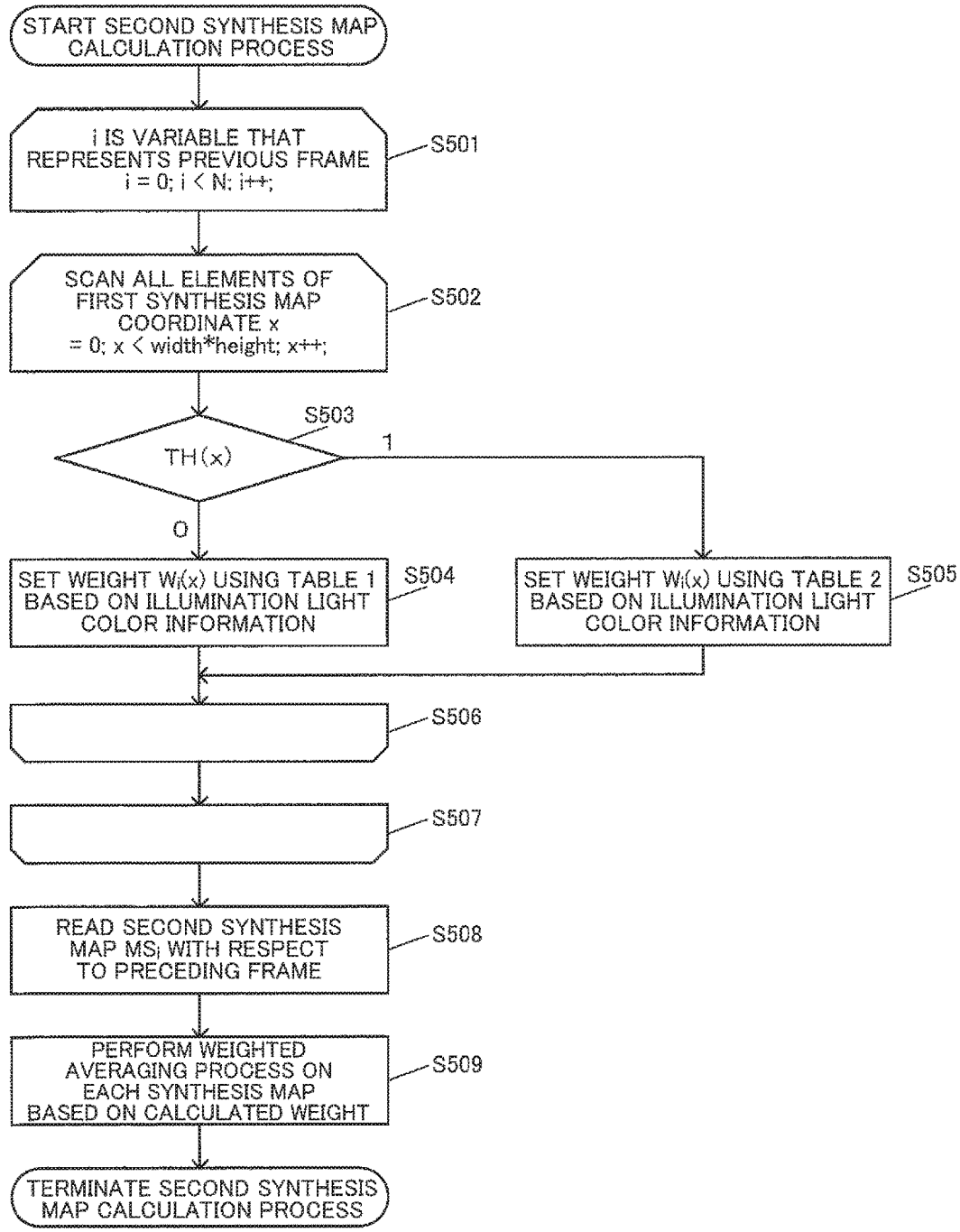
FIG. 17 is a flowchart illustrating a second synthesis map calculation process (third embodiment).

FIGS. 16 and 17 are flowcharts illustrating the process according to the third embodiment. FIG. 16 illustrates the process that is performed on a frame basis. The steps S401 to S403 illustrated in FIG. 16 are the same as the steps S101 to S103 illustrated in FIG. 9. After the frequency component has been calculated, the threshold value determination process is performed using the expression (7) to generate the threshold value determination map TH(x) (S404). The first synthesis map MF0 is calculated (S405), and the second synthesis map MS0 with respect to the current frame is calculated (S406).

FIG. 17 is a flowchart illustrating the second synthesis map (MS0) calculation process according to the third embodiment. The steps S501 and S502 illustrated in FIG. 17 are the same as the steps S201 and S202 illustrated in FIG. 10. In the third embodiment, the value of the threshold value determination map TH(x) is determined on a pixel basis (S503). When TH(x)=0, the weight Wi is set using the corresponding table (i.e., the table illustrated in FIG. 15A or 15C) (S504). When TH(x)=1, the weight Wi is set using the corresponding table (i.e., the table illustrated in FIG. 15B) that increases the degree of contribution of the current frame (S505). The steps S506 and S507 are end points of the loops that correspond to the steps S502 and S501.

When the weight has been set on a pixel basis (S507), the second synthesis map MS1 with respect the frame that immediately precedes the current frame is read from the frame memory (S508), and the first synthesis map MF0 with respect to the current frame calculated in the step S405 and the second synthesis map MS1 are synthesized using the weights set as described above to calculate the second synthesis map MS0 with respect to the current frame (S509).

When the second synthesis map MS0 with respect to the current frame has been calculated, the second synthesis map MS0 is stored in the frame memory (S407). The subsequent steps S408 to S411 are the same as the steps S107 to S110 illustrated in FIG. 9.

According to the third embodiment, the processing section 320 calculates the evaluation value from each of the plurality of captured images that were captured in the i-th frame and differ from each other as to the in-focus object plane position, and sets the weight information based on the result of the threshold value determination process that uses the calculated evaluation value and a given threshold value.

This makes it possible to determine whether or not the information obtained from the processing target frame is reliable based on the acquired images. More specifically, the process represented by the expression (7) is performed to calculate the threshold value determination map TH(x), and the weight Wi is set based on the calculated threshold value determination map TH(x).

The processing section 320 may set first weight information to a first area within the captured image for which it has been determined that the evaluation value is larger than the threshold value, calculate the second synthesis map used for the first area using the first weight information, set second weight information that differs from the first weight information to a second area within the captured image for which it has been determined that the evaluation value is equal to or smaller than the threshold value, and calculate the second synthesis map used for the second area using the second weight information.

This makes it possible to change the weight used for the second synthesis map calculation process corresponding to each area of the image based on the result of the threshold value determination process. More specifically, the process performed by the threshold value determination section 328 is performed on a pixel basis, the weight that is used for each pixel is determined (see the expression (7), and the steps S502 to S506 in FIG. 17). The first weight information is weight information that applies a large weight to the processing target frame, and corresponds to FIG. 15B, for example. The second weight information is weight information that applies a large weight to a frame other than the processing target frame, and corresponds to FIGS. 15A and 15C, for example. Note that the weight may be determined in a complex way taking account of an additional factor (see FIG. 15C). In such a case, the second weight information does not necessarily apply a large weight to a frame other than the processing target frame.

The processing section 320 may calculate the second synthesis map with respect to a j-th (wherein j is an integer that satisfies $1 \leq j \leq N$, $j \neq i$, and $j \neq k$) frame based on the first synthesis map calculated with respect to the j-th frame, and the second synthesis map calculated with respect to the i-th frame.

According to this configuration, when the second synthesis map with respect to a given frame (i-th frame) has been calculated by the process performed on the given frame, it is possible to use the second synthesis map that has been calculated when performing the process on the processing target frame (j-th frame). Since it is considered that the second synthesis map is highly reliable information that is based on the information obtained from a plurality of frames, it is possible to easily calculate the second synthesis map with respect to a different frame by utilizing the second synthesis map that has been calculated. For example, the process that calculates the second synthesis map from the first synthesis map may be performed in the same manner as in the first embodiment or the second embodiment during a certain period (e.g., first several frames or first cycle) after the process has started, and the calculated second synthesis map may be used during the subsequent process.

The j-th frame may be a frame that is temporally contiguous to the i-th frame. More specifically, the j-th frame may be a frame that immediately precedes or follows the i-th frame.

This makes it possible to designate a temporally close frame as the reference target with respect to the second synthesis map, and suppress the effect of a relative motion of the imaging section and the object, for example.

The first to third embodiments to which the invention is applied, and the modifications thereof, have been described above. Note that the invention is not limited to the first and to third embodiments and the modifications thereof. Various modifications and variations may be made of the first and to third embodiments and the modifications thereof without departing from the scope of the invention. A plurality of elements among the elements described above in connection with the first to third embodiments and the modifications thereof may be appropriately combined to implement various other configurations. For example, an arbitrary element may be omitted from the elements described above in connection with the first to third embodiments and the modifications thereof. Some of the elements described above in connection with the first to third embodiments and the modifications thereof may be appropriately combined. Any term cited with a different term having a broader meaning or the same meaning at least once in the specification and the drawings can be replaced by the different term in any place in the specification and the drawings. Specifically, various modifications and applications are possible without materially departing from the novel teachings and advantages of the invention.

What is claimed is:

1. An endoscope apparatus comprising:
    an imaging section having an optical system that can capture a plurality of images that differ from each other as to an in-focus object plane position, the imaging section performing a frame sequential imaging process while sequentially irradiating illumination lights that differ in spectral characteristics from an illumination section, and one cycle of the frame sequential imaging process including first to N-th (wherein N is an integer equal to or larger than 2) frames; and
    an image processing device, the imaging processing device comprising a processor comprising hardware, and the processor being configured to:
        acquire, from the imaging section, a plurality of captured images that have been captured by the imaging section in an i-th (wherein i is an integer that satisfies $1 \leq i \leq N$) frame and that differ from each other as to the in-focus object plane position;
        calculate a first synthesis map with respect to the i-th frame based on an evaluation value which represents an in-focus degree of each of the captured images in the plurality of captured images that have been captured in the i-th frame and that differ from each other as to the in-focus object plane position;
        acquire, from the imaging section, a plurality of captured images that have been captured by the imaging section in a k-th (wherein k is an integer that satisfies $1 \leq k \leq N$ and $k \neq i$) frame and that differ from each other as to the in-focus object plane position;
        calculate the first synthesis map with respect to the k-th frame based on an evaluation value which represents an in-focus degree of each of the captured images in the plurality of captured images that have been captured in the k-th frame and that differ from each other as to the in-focus object plane position;

calculate a second synthesis map including information that determines a pixel value of each pixel when synthesizing the plurality of captured images that have been captured in the i-th frame and that differ from each other as to the in-focus object plane position, based on the first synthesis map calculated with respect to the i-th frame, and the first synthesis map calculated with respect to the k-th frame that differs from the i-th frame;

generate an i-th synthesized image which brings an object that is distributed over a wider distance range than the plurality of captured images before being synthesized into focus, by performing a synthesis process which synthesizes the plurality of captured images that have been captured in the i-th frame and that differ from each other as to the in-focus object plane position based on the second synthesis map; and generate a color image by synthesizing first to N-th synthesized images that have been generated with respect to the first to N-th frames.

2. The endoscope apparatus as defined in claim 1, wherein the k-th frame temporally precedes the i-th frame.

3. The endoscope apparatus as defined in claim 1, wherein the processor calculates the second synthesis map with respect to the i-th frame by synthesizing the first synthesis map with respect to the i-th frame and the first synthesis map with respect to the k-th frame while weighting the first synthesis maps using given weight information.

4. The endoscope apparatus as defined in claim 3, wherein the processor calculates the second synthesis map using the weight information that increases a weight applied to the first synthesis map calculated with respect to a frame that is temporally close to the i-th frame.

5. The endoscope apparatus as defined in claim 3, wherein the processor calculates the evaluation value from each of the captured images that were captured in the i-th frame and that differ from each other as to the in-focus object plane position, and sets the weight information based on a result of a threshold value determination process that uses the calculated evaluation value and a given threshold value.

6. The endoscope apparatus as defined in claim 5, wherein the processor sets first weight information to a first area within the captured image for which it has been determined that the evaluation value is larger than the threshold value, calculates the second synthesis map used for the first area using the first weight information, sets second weight information that differs from the first weight information to a second area within the captured image for which it has been determined that the evaluation value is equal to or smaller than the threshold value, and calculates the second synthesis map used for the second area using the second weight information.

7. The endoscope apparatus as defined in claim 3, wherein the imaging section performs the frame sequential imaging process in which the one cycle includes an R frame, a G frame, and a B frame, and wherein the processor sets the weight information that increases a weight that is applied to the first synthesis map that corresponds to the G frame or the B frame as compared with the first synthesis map that corresponds to the R frame.

8. The endoscope apparatus as defined in claim 1, wherein the processor calculates the second synthesis map with respect to a j-th (wherein j is an integer that satisfies $1 \leq j \leq N$, $j \neq i$, and $j \neq k$) frame based on the first synthesis map calculated with respect to the j-th frame, and the second synthesis map calculated with respect to the i-th frame.

9. The endoscope apparatus as defined in claim 8, wherein the j-th frame is a frame that is temporally contiguous to the i-th frame.

10. The endoscope apparatus as defined in claim 1, wherein the processor calculates the second synthesis map with respect to the i-th frame based on the first synthesis map calculated with respect to the i-th frame, and the first synthesis maps calculated with respect to the first to (i−1)-th frames and (i+1)-th to N-th frames.

11. An endoscope apparatus comprising:

an imaging section having an optical system that can capture a plurality of images that differ from each other as to an in-focus object plane position, the imaging section performing a frame sequential imaging process in which one cycle includes first to N-th (wherein N is an integer equal to or larger than 3) frames that include at least an R frame, a G frame, and a B frame; and an image processing device, the image processing device comprising a processor comprising hardware, and the processor being configured to:

acquire, from the imaging section, a plurality of captured images that have been captured by the imaging section in an i-th (wherein i is an integer that satisfies $1 \leq i \leq N$) frame and that differ from each other as to the in-focus object plane position;

calculate a second synthesis map with respect to the i-th frame that corresponds to R based on a first synthesis map calculated with respect to a frame that corresponds to G and a first synthesis map calculated with respect to a frame that corresponds to B, when the i-th frame is a frame that corresponds to R, the second synthesis map including information that determines a pixel value of each pixel when synthesizing the plurality of captured images that have been captured in the i-th frame and that differ from each other as to the in-focus object plane position, and the first synthesis map being calculated based on an evaluation value which represents an in-focus degree of each of the captured images that have been captured in its corresponding frame;

generate an i-th synthesized image which brings an object that is distributed over a wider distance range than the plurality of captured images before being synthesized into focus, by performing a synthesis process which synthesizes the plurality of captured images that have been captured in the i-th frame and that differ from each other as to the in-focus object plane position based on the second synthesis map; and generate a color image by synthesizing first to N-th synthesized images that have been generated with respect to the first to N-th frames.

12. An image processing method comprising:

acquiring, from an imaging section having an optical system that can capture a plurality of images that differ from each other as to an in-focus object plane position, a plurality of captured images that have been captured by the imaging section in an i-th (wherein i is an integer that satisfies $1 \leq i \leq N$) frame and that differ from each other as to the in-focus object plane position, the imaging section performing a frame sequential imaging process while sequentially irradiating illumination lights that differ in spectral characteristics from an illumination section, and one cycle of the frame sequential imaging process including first to N-th (wherein N is an integer equal to or larger than 2) frames;

calculating a first synthesis map with respect to the i-th frame based on an evaluation value which represents an in-focus degree of each of the captured images in the plurality of captured images that have been captured in the i-th frame and that differ from each other as to the in-focus object plane position;

acquiring, from the imaging section, a plurality of captured images that have been captured by the imaging section in a k-th (wherein k is an integer that satisfies 1≤k≤N and k≠i) frame and that differ from each other as to the in-focus object plane position;

calculating the first synthesis map with respect to the k-th frame based on an evaluation value which represents an in-focus degree of each of the captured images in the plurality of captured images that have been captured in the k-th frame and that differ from each other as to the in-focus object plane position;

calculating a second synthesis map including information that determines a pixel value of each pixel when synthesizing the plurality of captured images that have been captured in the i-th frame and that differ from each other as to the in-focus object plane position, based on the first synthesis map calculated with respect to the i-th frame, and the first synthesis map calculated with respect to the k-th frame that differs from the i-th frame;

generating an i-th synthesized image which brings an object that is distributed over a wider distance range than the plurality of captured images before being synthesized into focus, by performing a synthesis process that synthesizes the plurality of captured images that have been captured in the i-th frame and that differ from each other as to the in-focus object plane position based on the second synthesis map; and generating a color image by synthesizing first to N-th synthesized images that have been generated with respect to the first to N-th frames.

13. An image processing method comprising:

acquiring, from an imaging section having an optical system that can capture a plurality of images that differ from each other as to an in-focus object plane position, a plurality of captured images that have been captured by the imaging section in an i-th (wherein i is an integer that satisfies 1≤i≤N) frame and that differ from each other as to the in-focus object plane position, the imaging section performing a frame sequential imaging process in which one cycle includes first to N-th (wherein N is an integer equal to or larger than 3) frames that include at least an R frame, a G frame, and a B frame;

calculating a second synthesis map with respect to the i-th frame that corresponds to R based on a first synthesis map calculated with respect to a frame that corresponds to G and a first synthesis map calculated with respect to a frame that corresponds to B, when the i-th frame is a frame that corresponds to R the second synthesis map including information that determines a pixel value of each pixel when synthesizing the plurality of captured images that have been captured in the i-th frame and that differ from each other as to the in-focus object plane position, and the first synthesis map being calculated based on an evaluation value which represents an in-focus degree of each of the captured images that have been captured in its corresponding frame;

generating an i-th synthesized image which brings an object that is distributed over a wider distance range than the plurality of captured images before being synthesized into focus, by performing a synthesis process that synthesizes the plurality of captured images that have been captured in the i-th frame and that differ from each other as to the in-focus object plane position based on the second synthesis map; and generating a color image by synthesizing first to N-th synthesized images that have been generated with respect to the first to N-th frames.

\* \* \* \* \*